United States Patent
Temelkuran et al.

(10) Patent No.: US 8,320,725 B2
(45) Date of Patent: Nov. 27, 2012

(54) PHOTONIC CRYSTAL FIBERS AND MEDICAL SYSTEMS INCLUDING PHOTONIC CRYSTAL FIBERS

(75) Inventors: Burak Temelkuran, Boston, MA (US); Charalambos Anastassiou, Malden, MA (US); David Torres, Stoughton, MA (US); Gil Shapira, Brookline, MA (US); Max Shurgalin, Lexington, MA (US); Gregor Dellemann, Cambridge, MA (US); Ori Weisberg, Cambridge, MA (US); Steven A. Jacobs, Needham, MA (US); Tairan Wang, Waltham, MA (US); Uri Kolodny, Cambridge, MA (US); Jesse Rusk, West Roxbury, MA (US); Robert Payne, Wellesley, MA (US); Yoel Fink, Brookline, MA (US)

(73) Assignee: OmniGuide, Inc., Cambridge, MA (US)

( * ) Notice: Subject to any disclaimer, the term of this patent is extended or adjusted under 35 U.S.C. 154(b) by 0 days.

(21) Appl. No.: 13/165,262

(22) Filed: Jun. 21, 2011

(65) Prior Publication Data

US 2011/0251603 A1 Oct. 13, 2011

Related U.S. Application Data

(63) Continuation of application No. 12/244,586, filed on Oct. 2, 2008, now Pat. No. 7,991,258, which is a continuation of application No. 11/584,167, filed on Oct. 20, 2006, now abandoned, which is a continuation of application No. 11/102,299, filed on Apr. 8, 2005, now Pat. No. 7,331,954.

(60) Provisional application No. 60/560,458, filed on Apr. 8, 2004, provisional application No. 60/561,020, filed on Apr. 9, 2004, provisional application No. 60/584,098, filed on Jun. 30, 2004, provisional application No. 60/628,462, filed on Nov. 16, 2004, provisional application No. 60/640,536, filed on Dec. 30, 2004, provisional application No. 60/658,531, filed on Mar. 4, 2005.

(51) Int. Cl.
*G02B 6/032* (2006.01)
*A61B 1/04* (2006.01)
*A61N 5/06* (2006.01)

(52) U.S. Cl. .......................... 385/125; 600/108; 607/89
(58) Field of Classification Search .................. 385/135, 385/50, 125; 607/80, 87–89
See application file for complete search history.

(56) References Cited

U.S. PATENT DOCUMENTS 3,467,098 A 9/1969 Ayers
(Continued)

FOREIGN PATENT DOCUMENTS

EP 1 198 904 5/1968
(Continued)

OTHER PUBLICATIONS

Temelkuran et al., "Wavelength-scalable hollow optical fibres with large photonic bandgaps for CO2 laser transmission", Nature, vol. 420, pp. 650-653 (2002).

(Continued)

*Primary Examiner* — Charlie Peng
(74) *Attorney, Agent, or Firm* — Goodwin Procter LLP

(57) ABSTRACT

In general, in one aspect, the disclosure features a system that includes a flexible waveguide having a hollow core extending along a waveguide axis and a region surrounding the core, the region being configured to guide radiation from the $CO_2$ laser along the waveguide axis from an input end to an output end of the waveguide. The system also includes a handpiece attached to the waveguide, wherein the handpiece allows an operator to control the orientation of the output end to direct the radiation to a target location of a patient and the handpiece includes a tip extending past the output end that provides a minimum standoff distance between the output end and the target location.

13 Claims, 10 Drawing Sheets

U.S. PATENT DOCUMENTS

| | | | |
|---|---|---|---|
| 3,659,915 A | 5/1972 | Maurer et al. | |
| 3,858,577 A | 1/1975 | Bass et al. | |
| 3,920,980 A | 11/1975 | Nath | |
| 4,076,380 A | 2/1978 | MiMarcello et al. | |
| 4,099,835 A | 7/1978 | French et al. | |
| 4,170,997 A | 10/1979 | Pinnow et al. | |
| 4,583,526 A | 4/1986 | Ali | |
| 4,652,083 A | 3/1987 | Laakmann | |
| 4,672,969 A | 6/1987 | Dew | |
| 4,688,892 A | 8/1987 | Laakmann | |
| 4,688,893 A | 8/1987 | Laakmann | |
| 4,805,987 A | 2/1989 | Laakmann et al. | |
| 4,806,289 A | 2/1989 | Laursen et al. | |
| 4,911,712 A | 3/1990 | Harrington | |
| 4,913,505 A | 4/1990 | Levy | |
| 4,917,084 A | 4/1990 | Sinofsky | |
| 4,930,863 A | 6/1990 | Croitoriu et al. | |
| 4,932,749 A | 6/1990 | Haidle et al. | |
| 4,947,540 A | 8/1990 | Komachi | |
| 5,002,051 A | 3/1991 | Dew et al. | |
| 5,005,944 A | 4/1991 | Laakmann et al. | |
| 5,030,217 A | 7/1991 | Harrington | |
| 5,044,717 A | 9/1991 | Levatter | |
| 5,061,265 A | 10/1991 | Abela et al. | |
| 5,062,842 A | 11/1991 | Tiffany | |
| 5,071,222 A | 12/1991 | Laakmann et al. | |
| 5,097,525 A | 3/1992 | Garcia et al. | |
| 5,136,676 A | 8/1992 | Arnett et al. | |
| 5,139,494 A | 8/1992 | Freiberg | |
| 5,140,984 A | 8/1992 | Dew et al. | |
| 5,147,354 A | 9/1992 | Boutacoff et al. | |
| 5,163,935 A | 11/1992 | Black et al. | |
| 5,257,991 A | 11/1993 | Fletcher et al. | |
| 5,276,761 A | 1/1994 | Shimoyama et al. | |
| 5,288,288 A | 2/1994 | Lewis et al. | |
| 5,304,171 A * | 4/1994 | Gregory et al. | 606/15 |
| 5,312,398 A | 5/1994 | Hobart et al. | |
| 5,325,458 A | 6/1994 | Morrow et al. | |
| 5,354,294 A | 10/1994 | Chou | |
| 5,380,317 A | 1/1995 | Everett et al. | |
| 5,423,805 A | 6/1995 | Brucker et al. | |
| 5,437,660 A | 8/1995 | Johnson et al. | |
| 5,440,664 A | 8/1995 | Harrington et al. | |
| 5,470,330 A | 11/1995 | Goldenberg et al. | |
| 5,471,553 A | 11/1995 | Teshima | |
| 5,480,050 A | 1/1996 | Morrow et al. | |
| 5,486,171 A | 1/1996 | Chou | |
| 5,489,256 A * | 2/1996 | Adair | 600/133 |
| 5,497,440 A | 3/1996 | Croitoru et al. | |
| 5,497,441 A | 3/1996 | Croitoru et al. | |
| 5,498,260 A | 3/1996 | Rink et al. | |
| 5,558,668 A | 9/1996 | Lankford et al. | |
| 5,567,471 A | 10/1996 | Harrington et al. | |
| 5,573,531 A | 11/1996 | Gregory | |
| 5,630,807 A | 5/1997 | Joffe | |
| 5,643,175 A | 7/1997 | Adair | |
| 5,729,646 A | 3/1998 | Miyagi et al. | |
| 5,735,844 A | 4/1998 | Anderson et al. | |
| 5,784,400 A | 7/1998 | Joannopoulos et al. | |
| 5,815,627 A | 9/1998 | Harrington | |
| 5,824,023 A | 10/1998 | Anderson | |
| 5,830,209 A | 11/1998 | Savage et al. | |
| 5,843,073 A | 12/1998 | Sinofsky | |
| 5,893,828 A | 4/1999 | Uram | |
| 5,935,491 A | 8/1999 | Tripathy et al. | |
| 5,951,543 A | 9/1999 | Brauer | |
| 5,995,696 A | 11/1999 | Miyagi et al. | |
| 6,104,853 A * | 8/2000 | Miyagi et al. | 385/125 |
| 6,130,780 A | 10/2000 | Joannopoulos et al. | |
| 6,141,476 A | 10/2000 | Matsuura et al. | |
| 6,165,205 A | 12/2000 | Neuberger | |
| 6,172,810 B1 | 1/2001 | Fleming et al. | |
| 6,306,130 B1 | 10/2001 | Anderson et al. | |
| 6,343,174 B1 | 1/2002 | Neuberger | 385/123 |
| 6,404,966 B1 | 6/2002 | Kawanishi et al. | |
| 6,463,200 B2 | 10/2002 | Fink et al. | |
| 6,496,632 B2 | 12/2002 | Borrelli et al. | |
| 6,527,764 B1 | 3/2003 | Neuberger et al. | |
| 6,547,780 B1 | 4/2003 | Sinofsky | |
| 6,563,981 B2 | 5/2003 | Weisberg et al. | |
| 6,571,045 B2 | 5/2003 | Hasegawa et al. | |
| 6,603,911 B2 | 8/2003 | Fink et al. | |
| 6,606,440 B2 | 8/2003 | Hasegawa et al. | |
| 6,625,364 B2 | 9/2003 | Johnson | |
| 6,683,277 B1 | 1/2004 | Millard et al. | |
| 6,723,090 B2 * | 4/2004 | Altshuler et al. | 606/9 |
| 6,728,439 B2 | 4/2004 | Weisberg et al. | |
| 6,735,369 B2 | 5/2004 | Komachi et al. | |
| 6,788,864 B2 | 9/2004 | Ahmad et al. | |
| 6,801,698 B2 | 10/2004 | King et al. | |
| 6,816,243 B2 | 11/2004 | Shurgalin et al. | |
| 6,856,742 B2 | 2/2005 | Broeng et al. | |
| 6,879,386 B2 | 4/2005 | Shurgalin et al. | |
| 6,895,154 B2 | 5/2005 | Johnson et al. | |
| 6,898,359 B2 | 5/2005 | Soljacic et al. | |
| 6,903,873 B1 | 6/2005 | Joannopoulos et al. | |
| 6,985,661 B1 | 1/2006 | Russell et al. | |
| 6,986,739 B2 | 1/2006 | Warren et al. | |
| 7,042,631 B2 | 5/2006 | Smith et al. | |
| 7,072,553 B2 | 7/2006 | Johnson et al. | |
| 7,099,533 B1 | 8/2006 | Chenard | |
| 7,142,756 B2 | 11/2006 | Anderson et al. | |
| 7,167,622 B2 | 1/2007 | Temelkuran et al. | |
| 7,190,875 B2 | 3/2007 | Anderson et al. | |
| 7,231,122 B2 | 6/2007 | Weisberg et al. | |
| 7,272,285 B2 | 9/2007 | Benoit et al. | |
| 7,310,466 B2 | 12/2007 | Fink et al. | |
| 7,311,962 B2 | 12/2007 | Fink et al. | |
| 7,331,954 B2 | 2/2008 | Temelkuran et al. | |
| 7,349,589 B2 | 3/2008 | Temelkuran et al. | |
| 2002/0150364 A1 | 10/2002 | Bassett et al. | |
| 2002/0193781 A1 | 12/2002 | Loeb | |
| 2003/0100824 A1 | 5/2003 | Warren et al. | |
| 2004/0013379 A1 | 1/2004 | Johnson et al. | |
| 2004/0068256 A1 | 4/2004 | Rizolu et al. | |
| 2004/0137168 A1 | 7/2004 | Fuflyigin | |
| 2004/0141702 A1 | 7/2004 | Fuflyigin et al. | |
| 2005/0008291 A1 * | 1/2005 | Baney | 385/31 |
| 2005/0271340 A1 * | 12/2005 | Weisberg et al. | 385/123 |
| 2006/0052661 A1 | 3/2006 | Gannot et al. | |
| 2011/0224661 A1 * | 9/2011 | Gille et al. | 606/16 |

FOREIGN PATENT DOCUMENTS

| | | |
|---|---|---|
| EP | 0 589 468 | 3/1994 |
| EP | 0 844 501 | 5/1998 |
| GB | 2 288 469 | 10/1995 |
| JP | 2003222740 | 8/2003 |
| WO | WO 85/01445 | 4/1985 |
| WO | WO 99/00062 | 1/1999 |
| WO | WO 99/47465 | 9/1999 |
| WO | WO 00/22466 | 4/2000 |
| WO | WO 00/43815 | 7/2000 |
| WO | WO 00/46287 | 8/2000 |
| WO | WO 02/41050 | 5/2002 |
| WO | WO 02/061467 | 8/2002 |
| WO | WO 02/072489 | 9/2002 |
| WO | 03/050571 | 6/2003 |
| WO | WO 03/079073 | 9/2003 |
| WO | WO 03/079077 | 9/2003 |
| WO | WO 2004/052078 | 6/2004 |
| WO | WO2004058328 A2 | 7/2004 |
| WO | WO 2004/064623 | 8/2004 |

OTHER PUBLICATIONS

European Search Report for Application No. / Patent No.—03796927.6 / PCT/US0339344, dated May 12, 2006.

Allan et al. "Photonic crystal fibers: effective-index and band-gap guidance." Photonic Crystals and Light Localization in the 21$^{st}$ Century. 2001: Kluwer. pp. 305-320.

Anastassiou, C., G. Dellemann, O. Weisberg, U. Kolodny, "Fiber Deliver C)2 Laser Beams for Medical Applications", Photonics Spectra, Mar. 2004.

Barkou et al. "Silica-air photonic crystal fiber design that permits waveguiding by a true photonic bandgap effect." Optics Letters, 24:1, Jan. 1, 1999, pp. 46-48.

Baumeister, P. "The transmission and degree of polarization of quarter-wave stacks at non-normal incidence." Opt. Acta, 8, 1961, pp. 105-119.

Birks et al. "Full 2-D photonic bandgaps in silica/air structures." Electronic Letters, 31:22, Oct. 26, 1995, pp. 1941-1943.

Bormashenko et al. "Development of new-near-infrared filters based on the 'sandwich' polymer-chalcogenide glass-polymer composites." Optical Engineering, 40:5, 2001, pp. 661-662.

Bormashenko et al. "New Oriented Polymer/Thermoplastic Glass Composites for IR Optics." Engineering Materials, 10, 2000, pp. 657-658.

Bormashenko et al. "Optical Properties and infrared optics applications of composite films based on polyethylene and low-melting-point chalcogendie," Society of Photo-Optical Instrumentation Engineers, Feb. 2002. pp. 295-302.

Bornstein et al. "Chalcogenide Hollow Fibers," Journal of Non-Crystalline Solids, 77:8, 1985, pp. 1277-1280.

Broeng et al. "Analysis of air-guiding photonic bandgap fibers." Optics Letters, 25:2, 2000, pp. 96-98.

Cregan et al. "Single-Mode Photonic Band Gap Guidance of Light in Air." Science, 285, Sep. 3, 1999, pp. 1537-1539.

Dai et al. "High-peak-power, pulsed $CO_2$ laser light delivery by hollow glass waveguides." Appl Optics, 36, 1997, pp. 5072-5077.

De Sterke et al. "Differential losses in Bragg fibers." J. Appl. Phys., 76:2, Jul. 15, 1994, pp. 680-688.

Eggleton et al. Microstructured optical fiber devices. Optics Express, 9:13, 2001, pp. 698-713.

Feigel A. et al. "Chalcogenide glass-based three-dimensional photonic crystals." Applied Physics Letters, 77:20, pp, 3221-3223, Nov. 13, 2000.

Fink et al. "A dielectric omnidirectional reflector." Science, 282:5394, 1998, pp. 1679-1682.

Fink et al. "Guiding Optical Light in Air Using an All-Dielectric Structure." Journal of Lightwave Technology, 17:11, Nov. 11, 1999, pp. 2039-2041.

Fitt et al. "Modeling the fabrication of hollow fibers: Capillary drawings." Journal of Lightwave Technology, 19:12, 2001, pp. 1924-1931.

Gopal et al. "Deposition and characterization of metal sulfide dielectric coatings for hollow glass waveguide." Optical Society of America, 2003. Optics Express, 11:24, Dec. 1, 2003.

Harrington, J.A. "Infrared Fibers in Handbook of Optics." McGraw-Hill, 2001, pp. 14, 1-14, 13.

Harrington, James. "A Review of IR Transmitting, Hollow Waveguides." Fiber and Integrated Optics, 19, 2000, pp. 211-217.

Hart et al, "External Reflection from Omnidirectional Dielectric Mirror Fibers." Science, 296, Apr. 19, 2002, pp. 510-513.

Hilton, A.R., "Optical Properties of Chalcogenide Glasses." Journal of Non-Crystalline Solids, 2, 1970, pp. 28-39.

Hongo et al, "Transmission of Kilowatt-Class Co2-Laser Light through Dielectric-Coated Metallic Hollow Wave-Guides for Material Processing," Applied Optics, 31:24, 1992. pp. 5114-5120.

Ibanescu et al. "An all-dielectric coaxial waveguide." Science, 289:5478, 2000, pp. 415-419.

Ibanescu et al. "Analysis of Mode Structure in OmniGuide Fibers." Physical Review E, 67:4, 2003.

Ivanenko et al. "In vitro incision of bone tissue with a Q-switch $CO_2$ laser. Histological examination." Lasers in the Life Sciences, vol. 9, pp. 171-179 (2000).

John F. Ready "4.8 Process Gas Nozzles—Chapter 4: Components for Laser Materials Processing Systems" LIA Handbook of Laser Materials Processing, pp. 155-159 (2001).

John, S. "Strong Localization of Photons in Certain Disordered Dielectric Superlattices." Physical Review Letters, 58:23, 1987, pp. 2486-2489.

Johnson et al. "Low-loss asymptotically single-mode propagation in large-core OmniGuide fibers." Optics Express, 9:13, 2001, pp. 748-779.

Keck et al. "On the ultimate lower limit of attenuation in glass optical waveguides." Applied Physics Letters, 22:7, 1973, pp. 307-309.

King et al "Laboratory preparation of highly pure $As_2Se_3$ glass." J. Non-Cryst, Sol., 181, 1995, pp. 231-237.

Knight et al. "Photonic Band Gap Guidance in Optical Fibers," Science, 282, Nov. 20, 1998, pp. 1476-1478.

Kucuk et al. "An estimation of the surface tension for silicate glass melts at 1400° C using statistical analysis." Glass Technol., 40, 1999, pp. 149-153.

Mahlein, Generalized Brewster-angle conditions for quarter-wave multilayers at non-normal incidence. J. Opt. Soc. Am., 64, 1974, pp. 647-653.

Marcatilli et al. "Hollow metallic and dielectric waveguides for long distance optical transmission and lasers." Bell Syst. Tech, J., 43, 1964, pp. 1783-1809.

Mossadegh R. et al. "Fabrication of single-mode chalcogenide optial fiber," Journal of Lightwave Technology, 16:2, pp. 214-216, Feb. 1998.

Matsuura et al. "Hollow infrared fibers fabricated by glass-drawing technique." Optics Express, 10:12, 2002, pp. 488-492.

Matsuura et al. "Small-bore hollow waveguide for delivery of near singlemode IR laster radiation." Electronic Letters, 30, 1994, pp. 1688-1690.

Mitra et al. "Nonlinear limits to the information capacity of optical fibre communications." Nature, 411, 2001, pp. 1027-1030.

Miyagi et al. "Design Theory of Dielectric-Coated Circular Metallic Waveguides for Infrared Transmission." Journal of Lightwave Technology, 2:2, 1984, pp. 116-126.

Monro, T.M. et al. "Chalcogenide Holey Fibres." Electronics Letters, 36:24, pp. 1998-2000, Nov. 23, 2000.

Nishii, J. et al. "Chalcogenide glass fiber with a core-cladding structure." Applied Optics, 28; 23, pp. 5122-5127, Dec. 1, 1989.

Nubling et al. "Hollow-waveguide delivery systems for high-power, industrial $CO_2$ lasers," Applied Optics, 34:3, Jan. 20, 1996, pp. 372-380.

Ouyang et al. "Comparitive study of air-core and coaxial Bragg fibers: single-mode transmission and dispersion characteristics," Optics Express, 9:13, 2001, pp. 733-747.

Pottage et al. "Robust photonic band gaps for hollow core guidance in PCF made from high index glass." Optics Express, 11:22, Nov. 3, 2003, pp. 2854-2861.

Renn et al. "Laser-Guided Atoms in Hollow-Core Optical Fibers." Physical Review Letters, 75:18, 1995, pp. 3253-3256.

Rundquist et al. "Phase-matched generation of coherent soft-X-rays," Science, 280:5368, 1998, pp. 1412-1415.

Sanghera et al. "Active and passive chalcogenide glass optical fibers for IR applications: a review," Journal of Non-Crystalline Solids, 257, 1999, pp. 6-16.

Sanghera, J.S. et al. "Fabrication of long lengths of low-loss IR transmitting AS40S (60-X) sex glass fibers," Journal of Lightwave Technology, 14:5, pp. 743-748, May 1, 1996.

Seddon, A.B. "Chalcogenide glasses: a review of their preparation, properties and applications," J. Non-Cyrst. Sol., 184, 1995, pp, 44-50.

Temelkuran et al. "Wavelength-scalable hollow optical fibres with large photonic bandgaps for $CO_2$ laser transmission." Nature, 420, Dec. 12, 2002, pp. 650-653.

Temelkuran et al, "Low-loss infrared dielectric materials system for broadband dual-rang omnidirectional reflectivity," Optics Letters, 26, 2001, pp. 1370-1372.

Torres et al, "OmniGuide Photonic Bandgap Fibers for flexible Delivery of $CO_2$ Lasers in Laryngology" Proceedings of SPIE, vol. 5686, pp. 310-321 (Apr. 2005).

Varsheneya A.K. Fundamentals of Inorganic Glasses, Academic Press, San Diego, pp. 5-7,1994.

Varshneya, A. K. "Some comments on physical properties of chalcogenide glasses." J. Non-Cryst. Sol., 273, 2000, pp. 1-7.

Vienne et al, "First demonstration of air-silica Bragg fiber," Optical Society of America, 2003, Institute of Electrical and Electronics Engineers, Optical Fiber Communication Conference and Exposition Postdeadline Papers.

Weber et al, Giant Birefringent Optics in Multilayer Polymer Mirrors, Science, 287, 2000, pp. 2451-2456.

Winn et al. Omnidirectional reflection from a one-dimensional photonic crystal. Optics Letters, 23, 1998, pp. 1573-1575.

Yablonovitch. E. "Inhibited Spontaneous Emission in Solid-State Physics and Electronics." Physical Review Letters, 58:20, 1987, pp. 2059-2062.

Yeh et al. "Theory of Bragg Fiber." Journal of the Optical Society of America, 68:9, 1978, pp. 1196-1201.

Yeh et al. Electromagnetic propagation in periodic stratified media, I. General theory, J. Opt. Soc. Am., 67, 1977, pp. 423-438.

Search report, Oct. 27, 2005, PCT/US05/12047.

Sanghera et al. "Development and Infrared Applications of Chalcogenide Glass Optical Fibers." Fiber and Integrated Optics, 19:251, 2000, pp. 251-274.

"Hollow Fibers for Infrared Laser Light Transmission", Hitachi Cable Review No. 23, Aug. 2004.

Akihito Hongo et al., "Infrared Hollow Fibers for Medical Applications", Hitachi Cable Review No. 23, Aug. 2004.

* cited by examiner

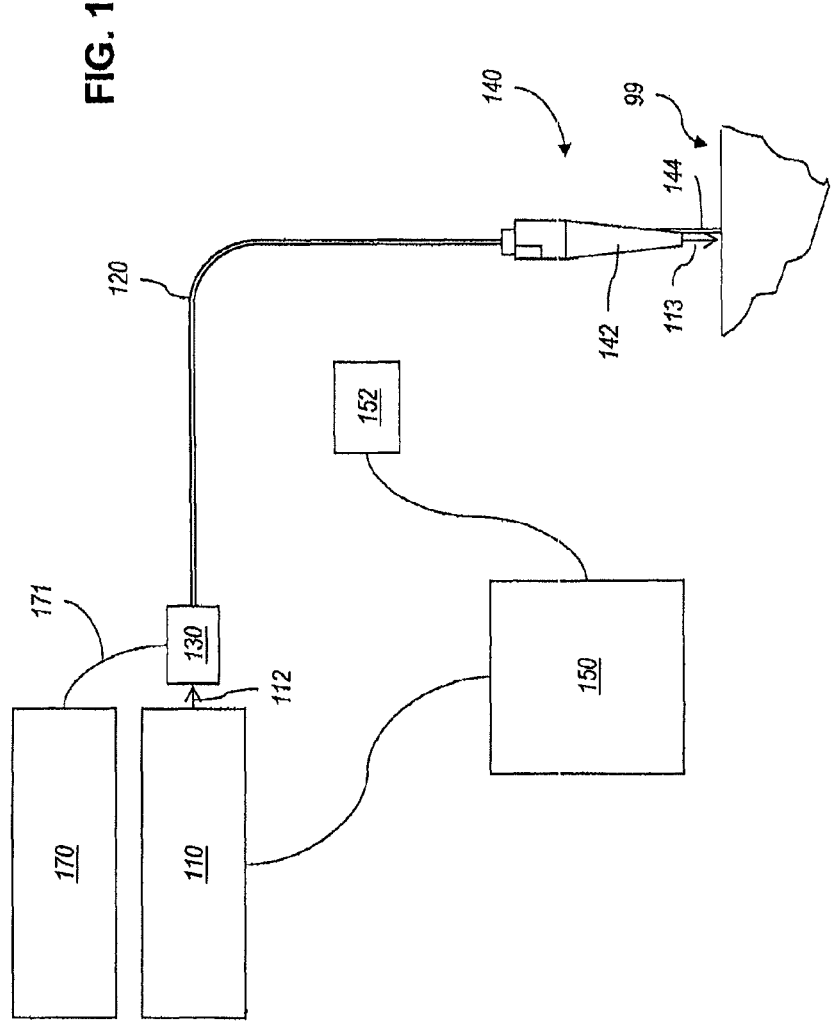

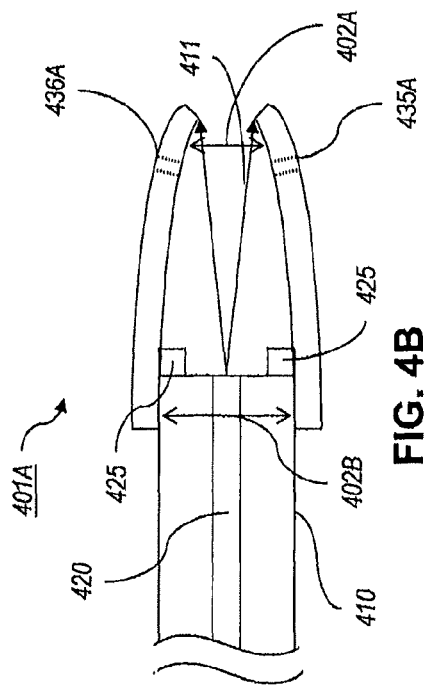
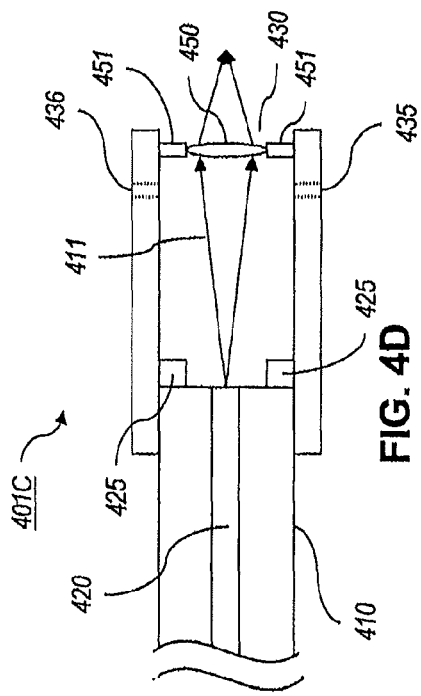
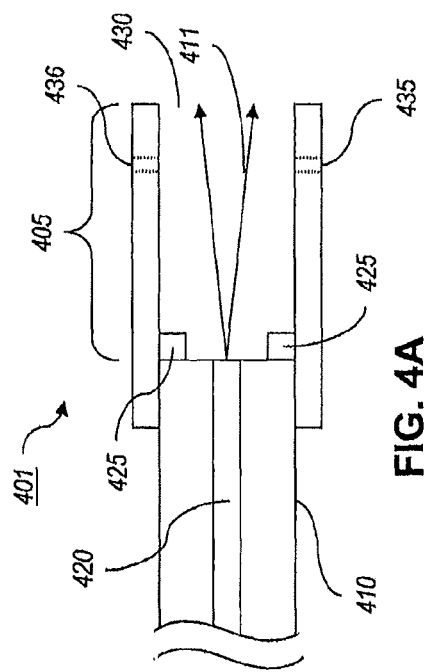
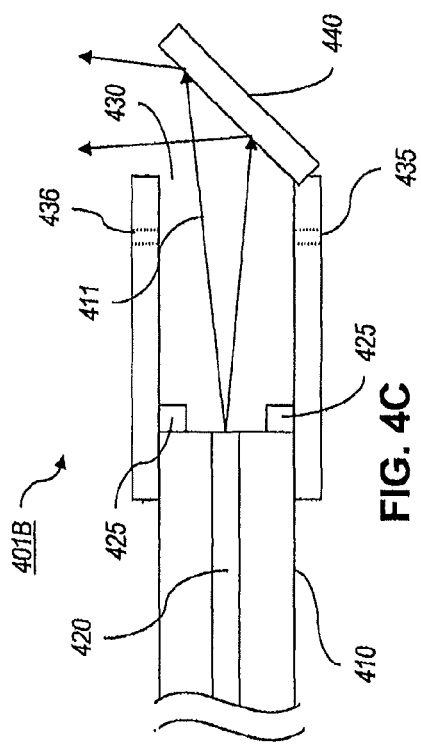

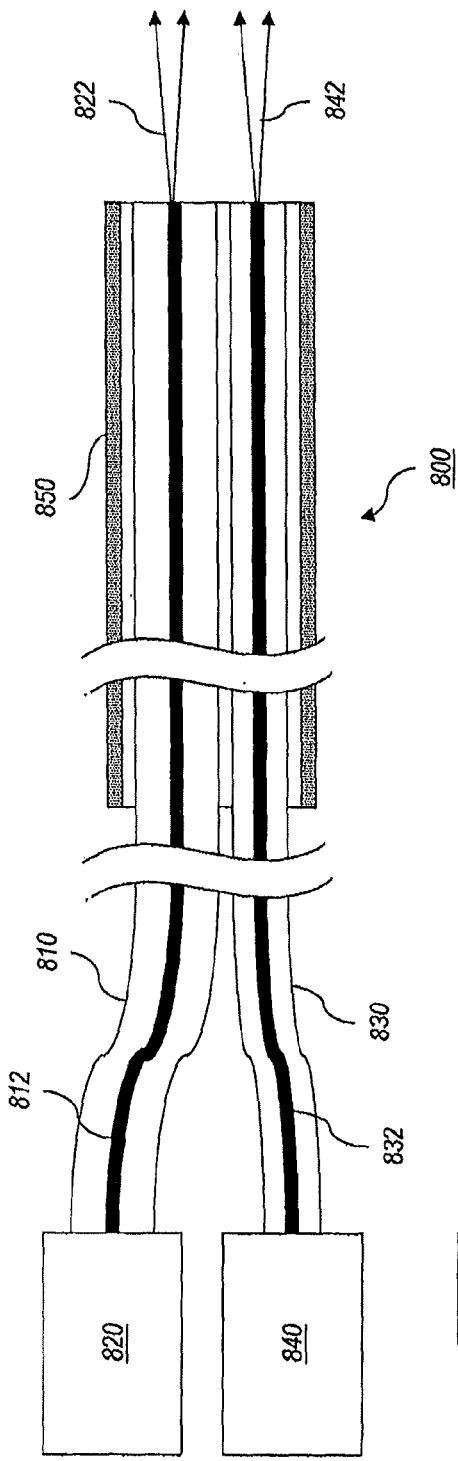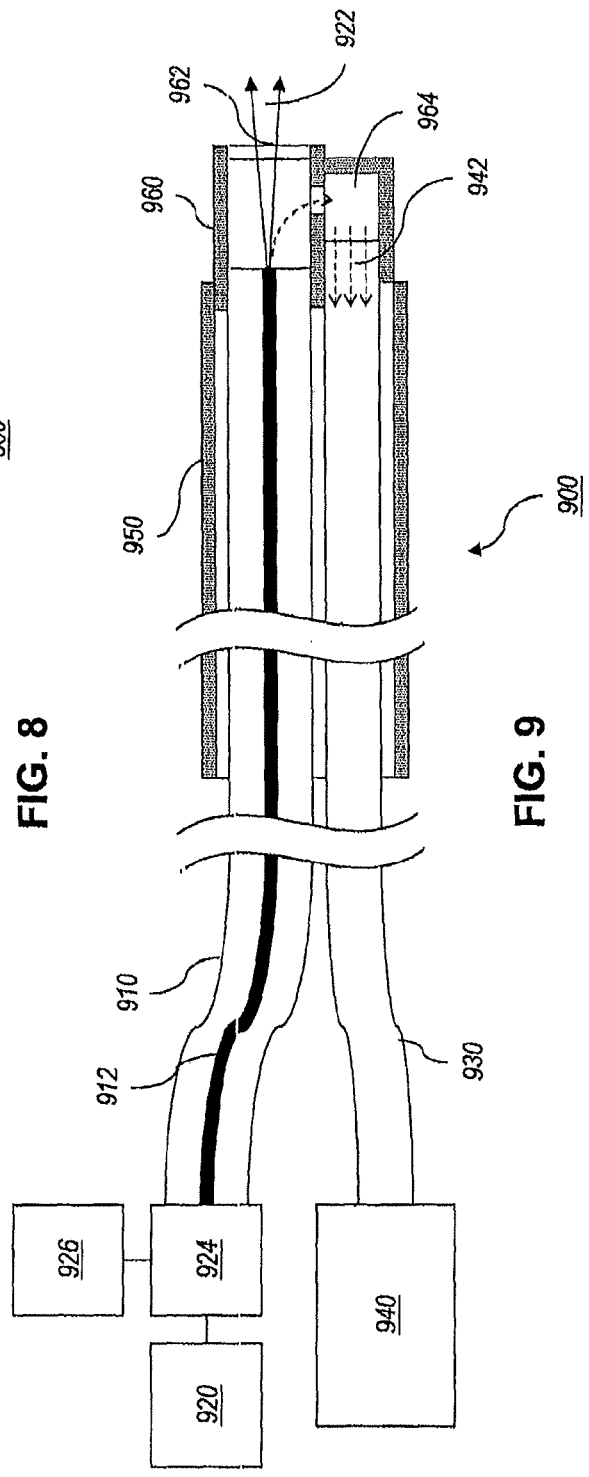

PHOTONIC CRYSTAL FIBERS AND MEDICAL SYSTEMS INCLUDING PHOTONIC CRYSTAL FIBERS

CROSS-REFERENCE TO RELATED APPLICATIONS

This application is a continuation of U.S. patent application Ser. No. 12/244,586, filed on Oct. 2, 2008, which is a continuation of U.S. patent application Ser. No. 11/584,167, filed on Oct. 20, 2006, now abandoned, which is a continuation of U.S. patent application Ser. No. 11/102,299, filed on Apr. 8, 2005, issued as U.S. Pat. No. 7,331,954, on Feb. 19, 2008, which claims the benefit of priority to Provisional Patent Application 60/560,458, entitled "PHOTONIC CRYSTAL FIBER APPLICATIONS," filed on Apr. 8, 2004, Provisional Patent Application 60/561,020, entitled "PHOTONIC CRYSTAL FIBER APPLICATIONS," filed on Apr. 9, 2004, Provisional Patent Application 60/584,098, entitled "PHOTONIC CRYSTAL FIBER APPLICATIONS," filed on Jun. 30, 2004, Provisional Patent Application 60/628,462, entitled "PHOTONIC CRYSTAL FIBER APPLICATIONS," filed on Nov. 16, 2004, Provisional Patent Application 60/640,536, entitled "OMNIGUIDE PHOTONIC BANDGAP FIBERS FOR FLEXIBLE DELIVERY OF $CO_2$ LASERS IN LARYNGOLOGY," filed on Dec. 30, 2004, and Provisional Patent Application 60/658,531, entitled "PHOTONIC CRYSTAL FIBERS," filed on Mar. 4, 2005. The contents of all the above-listed patent applications are hereby incorporated by reference in their entirety.

BACKGROUND

Lasers are prevalent in many areas of medicine today. For example, lasers find application in diverse medical areas, such as surgery, veterinary medicine, dentistry, ophthalmology, and in aesthetic medical procedures.

In many of these applications, an optical fiber is used to deliver radiation from a laser to the target region of the patient. Conventional optical fibers are excellent waveguides for radiation having wavelengths in the visible or near-infrared portion of the electromagnetic spectrum (e.g., wavelengths of about 2 microns or less). However, conventional optical fibers are, in general, not suitable in applications where high power laser radiation with relatively long wavelengths is used. Accordingly, many medical laser systems that deliver high power (e.g., about 10 Watts or more), long wavelength (e.g., greater than about 2 microns), do so using an articulated arm that includes optical components that guide the laser radiation through rigid conduits or free space from the laser to the target.

SUMMARY

Photonic crystal fibers can be used in medical laser systems to guide radiation from a radiation source (e.g., a laser) to a target location of a patient. In general, photonic crystal fibers include a region surrounding a core that provides extremely effective confinement of certain radiation wavelengths to the core. These so-called confinement regions can be formed exclusively from amorphous dielectric materials (e.g., glasses and/or polymers), and can provide effective confinement while still being relatively thin. Accordingly, photonic crystal fibers can include thin, flexible fiber's capable of guiding extremely high power radiation.

Moreover, photonic crystal fibers can be drawn from a preform, resulting in fibers that are relatively inexpensive to produce compared to other waveguides that are not drawn. Fiber manufacturing techniques also provides substantial production capacity, e.g., thousands of meters of fiber can be drawn from a single preform. The conversion in the draw process from a relatively short preform to very long lengths of fiber can effectively smooth out any perturbations from the desired structure that exist in the preform, producing low-loss, low-defect fiber.

In general, in a first aspect, the invention features systems, including a photonic crystal fiber including a core extending along a waveguide axis and a dielectric confinement region surrounding the core, the dielectric confinement region being configured to guide radiation along the waveguide axis from an input end to an output end of the photonic crystal fiber. The systems also includes a handpiece attached to the photonic crystal fiber, wherein the handpiece allows an operator to control the orientation of the output end to direct the radiation to a target location of a patient.

Embodiments of the systems can include one or more of the following features and/or aspects of other aspects.

The handpiece can include an endoscope. The endoscope can include a flexible conduit and a portion of the photonic crystal fiber is threaded through a channel in the flexible conduit. The endoscope can include an actuator mechanically coupled to the flexible conduit configured to bend a portion of the flexible conduit thereby allowing the operator to vary the orientation of the output end. The actuator can be configured to bend the portion of the flexible conduit so that the bent portion of the flexible conduit has a radius of curvature of about 12 centimeters or less (e.g., about 10 centimeters or less, about 8 centimeters or less, about 5 centimeters or less, about 3 centimeters or less). The actuator can be configured to bend the flexible conduit within a bend plane. The handpiece can be attached to the photonic crystal fiber to maintain an orientation of the dielectric confinement region to control the orientation of the photonic crystal fiber about its waveguide axis within the flexible conduit. The attachment between the handpiece and the photonic crystal fiber can prevent twisting of the fiber by more than about 10 degrees (e.g., by more than about 5 degrees) while maintaining operation. The endoscope can further include an auxiliary conduit including a first portion coupled to the flexible conduit, wherein the photonic crystal fiber is threaded through a channel in the auxiliary conduit into the channel of the flexible conduit, the auxiliary conduit further comprising a second portion moveable with respect to the first portion, wherein the photonic crystal fiber is attached to the second portion and moving the second portion allows the operator to extend or retract the output end relative to an end of the flexible conduit. The second portion can extend or retract with respect to the first portion. The auxiliary conduit can be a rigid conduit.

In some embodiments, the handpiece includes a conduit and a portion of the photonic crystal fiber is threaded through the conduit. The conduit can include a bent portion. The conduit can be formed from a deformable material. The handpiece can further include an actuator mechanically coupled to the conduit configured to bend a portion of the conduit thereby allowing the operator to vary the orientation of the output end.

The handpiece can include a tip extending past the output end that provides a minimum standoff distance of about 1 millimeter or more between the output end and the target location.

The photonic crystal fiber can be sufficiently flexible to guide the radiation to the target location while a portion of the photonic crystal fiber is bent through an angle of about 90 degrees or more and the portion has a radius of curvature of about 12 centimeters or less. The radiation can have an average power at the output end of about 1 Watt or more while the portion of the photonic crystal fiber is bent through an angle of about 90 degrees or more and the portion has a radius of curvature of about 12 centimeters or less. The radiation can have an average power at the output end of about 5 Watts or more while the portion of the photonic crystal fiber is bent through an angle of about 90 degrees or more and the portion has a radius of curvature of about 12 centimeters or less. The photonic crystal fiber can be sufficiently flexible to guide the radiation to the target location while the portion of the photonic crystal fiber is bent through an angle of about 90 degrees or more and the portion has a radius of curvature of about 10 centimeters or less (e.g., about 5 centimeters or less).

The dielectric confinement region can include a layer of a first dielectric material arranged in a spiral around the waveguide axis. The dielectric confinement region can further include a layer of a second dielectric material arranged in a spiral around the waveguide axis, the second dielectric material having a different refractive index from the first dielectric material. The first dielectric material can be a glass (e.g., a chalcogenide glass). The second dielectric material can be a polymer. The dielectric confinement region can include at least one layer of a chalcogenide glass. The dielectric confinement region can include at least one layer of a polymeric material. In some embodiments, the dielectric confinement region includes at least one layer of a first dielectric material extending along the waveguide axis and at least one layer of a second dielectric material extending along the waveguide axis, wherein the first and second dielectric materials can be co-drawn with the first dielectric material.

The core can be a hollow core. The system can further include a fluid source coupled to the input end or output end, wherein during operation the fluid source supplies a fluid through the core. The fluid can be a gas.

The core can have a diameter of about 1,000 microns or less (e.g., about 500 microns or less). The photonic crystal fiber can have an outer diameter of about 2,000 microns or less at the output end.

In some embodiments, the system further includes an optical waveguide and a connector that attaches the optical waveguide to the photonic crystal fiber. The optical waveguide can be a second photonic crystal fiber. The system can also include a conduit surrounding the optical waveguide. The conduit can be more rigid than the optical waveguide. The system can include a fluid source coupled to the conduit and wherein during operation the fluid source supplies a fluid to the conduit.

The system can further include a laser to produce the radiation and direct it towards the input end of the photonic crystal fiber. The laser can be a $CO_2$ laser. The radiation can have a wavelength of about 2 microns or more. In some embodiments, the radiation has a wavelength of about 10.6 microns.

In certain embodiments, the system further includes an auxiliary radiation source and at least one additional fiber mechanically coupled to the photonic crystal fiber, the additional waveguide being configured to deliver auxiliary radiation from the auxiliary radiation source to the target location. The additional fiber can be mechanically coupled to the photonic crystal fiber by the handpiece. The auxiliary radiation source can be a second laser, different from the laser positioned to direct the radiation to the input end of the photonic crystal fiber. The second laser can be an Nd:YAG laser, a diode laser, or a pulsed dye laser. The auxiliary radiation can have a wavelength in the visible portion of the electromagnetic spectrum.

At least a portion of the photonic crystal can be sterilized.

In general, in another aspect, the invention features articles that include a length of a photonic crystal fiber, the photonic crystal fiber including a core extending along a waveguide axis and a dielectric confinement region surrounding the core, the dielectric confinement region being configured to guide radiation along the waveguide axis from an input end to an output end of the photonic crystal fiber, wherein the length of the photonic crystal fiber is sterilized.

The articles can further include a sealed package containing the length of the photonic crystal fiber. Embodiments of the articles can include one or more of the features of other aspects.

In general, in a further aspect, the invention features methods that include directing radiation into an input end of a photonic crystal fiber and using a handpiece attached to the photonic crystal fiber to control the orientation of an output end of the photonic crystal fiber and direct radiation emitted from the output end towards a target location of a patient. Embodiments of the methods can include one or more of the features of other aspects.

In general, in another aspect, the invention features methods that include directing radiation to a target location of a patient through a photonic crystal fiber, the photonic crystal fiber having a hollow core and flowing a fluid through the hollow core to the target location of the patient.

Embodiments of the methods can include one or more of the following features and/or features of other aspects.

The radiation can have sufficient power to incase, excise, or ablate tissue at the target location. The fluid can have a sufficient pressure and temperature to coagulate blood at the target location.

The methods can include bending the photonic crystal fiber while directing the radiation and the fluid to the target location. Bending the fiber can include bending a portion of the fiber through about 45° or more to have a radius of curvature of about 12 centimeters or less.

Directing the radiation and the fluid to the target location can include holding a portion of a handpiece attached to the photonic crystal fiber and controlling the orientation of the output end using the handpiece.

The fluid can be a gas, a liquid, or a superfluid. In embodiments where the fluid is gas, the gas can have a pressure of about 0.5 PSI or more (e.g., about 1 PSI or more) at the output end. The gas can have a temperature of about 50° C. or more (e.g., about 80° C. or more) at the target location. The gas can be air. The gas can include carbon dioxide, oxygen, nitrogen, helium, neon, argon, krypton, or xenon. The gas can be a substantially pure gas. For example, the gas can include about 98% or more of a single component gas. Alternatively, in some embodiments, the gas is gas mixture.

The fluid can be flowed into the hollow core at a rate of about 1 liter per minute or more (e.g., about 2 liters per minute or more, about 5 liters per minute or more, about 8 liters per minute or more).

The radiation can have a wavelength of about 2 microns or more (e.g., about 10.6 microns). The radiation can have an average power of about 1 Watt or more at the target location.

In general, in a further aspect, the invention features apparatus that include a photonic crystal fiber including a core extending along a waveguide axis and a dielectric confinement region surrounding the core, the dielectric confinement region being configured to guide radiation along the waveguide axis from an input end to an output end of the photonic crystal fiber, and a sleeve coupled to the output end of the photonic crystal fiber to allow the radiation to pass through the sleeve and exit the sleeve through a primary opening, the sleeve further comprising one or more secondary openings positioned so that gas flowed into the sleeve exits the sleeve through the secondary openings.

Embodiments of the apparatus can include one or more of the following features and/or features of other aspects.

The gas flowed into the sleeve can exit the sleeve through the primary opening in addition to through the secondary openings. The apparatus can further include a transparent element positioned between the primary opening and the secondary openings that substantially transmits the radiation as it passes through the sleeve. The transparent element can substantially prevent gas from exiting the sleeve through the primary opening. The transparent element can include ZnSe.

The apparatus can further include a conduit positioned relative to the secondary opening so that gas exiting the sleeve through the secondary opening is drawn into an input end of the conduit.

The secondary opening can be positioned near to the primary opening. The primary opening can have a diameter that is smaller than an outer diameter of the photonic crystal fiber at the output end. The apparatus can further include a focusing element attached to the sleeve to focus the radiation passing through the sleeve. Alternatively, or additionally, the can include a reflecting element attached to the sleeve to reflect the radiation passing through the sleeve.

In general, in another aspect, the invention features apparatus that include an assembly including a radiation input port configured to receive radiation from a radiation source and an output port configured to couple the radiation to a photonic crystal fiber, the assembly further including a retardation element positioned to modify a polarization state of the radiation received from the radiation source before it is coupled to the photonic crystal fiber.

Embodiments of the apparatus can include one or more of the following features and/or features of other aspects.

The assembly can further include a gas input port configured to receive gas from a gas source. The photonic crystal fiber can have a hollow core. The output port can be further configured to couple the gas received from the gas source into the hollow core of the photonic crystal fiber. The apparatus can include the gas source.

The retardation element can be a reflective retardation element. The apparatus can include the radiation source, wherein the radiation from the radiation source includes radiation having a wavelength $\lambda$. The reflective retardation element can include a mirror and a retardation layer having an optical thickness of about $\lambda$ or less disposed on a surface of the mirror. The retardation layer can have an optical thickness of about $\lambda/4$ along a direction about 45° relative to a normal to the surface of the mirror. A, can be about 2 microns or more. For example, $\lambda$ can be about 10.6 microns.

The retardation element can be a transmissive retardation element.

The retardation element can modify the polarization state of the radiation from a substantially linear polarization state to a substantially non-linear polarization state. The substantially non-linear polarization state can be a substantially circular polarization state.

The assembly can further include a focusing element configured to focus the radiation entering the assembly at the radiation input port to a waist near the output port. The focusing element can focus the radiation to a waist diameter of about 1,000 microns or less (e.g., about 500 microns or less). The focusing element can be a lens. The lens can include ZnSe.

The apparatus can further include the photonic crystal fiber.

In general, in another aspect, the invention features methods that include modifying a polarization state of radiation emitted from a laser, directing the radiation having the modified polarization state into an input end of a photonic crystal fiber having a hollow core, and coupling gas from a gas source into the input end of the hollow core.

Embodiments of the methods can include one or more of the features or other aspects.

In general, in another aspect, the invention features methods that include guiding radiation through an optical waveguide to tissue of a patient, wherein the optical waveguide has a hollow core, and directing gas to the tissue while guiding the radiation, wherein the radiation and gas are sufficient to cut (e.g., excise or ablate) the tissue and to substantially coagulate exposed blood.

In general, in a further aspect, the invention features a medical laser system, including a laser, an optical waveguide having a hollow core, a delivery device, a gas source (e.g., a cylinder of gas, a compressor, a blower) configured to deliver a gas to the tissue, wherein during operation radiation from the laser and gas from the gas source are delivered to tissue of a patient, wherein the radiation and gas are sufficient to incise the tissue and substantially coagulate exposed blood.

In general, in another aspect, the invention features a system, including a laser having an output terminal, a photonic crystal fiber having an input end and an output end, the input end being configured to accept radiation emitted from the output terminal, and a delivery device for allowing an operator to direct radiation emitted from the output end to target tissue.

In general, in another aspect, the invention features a system, including a $CO_2$ laser, an endoscope, and a photonic crystal fiber, wherein during operation the photonic crystal fiber guides radiation from the $CO_2$ laser through the endoscope to target tissue.

In general, in a further aspect, the invention features a coupler for coupling gas and radiation into one end of a hollow core of a fiber.

Embodiments of the invention may include one or more of the following features.

The gas can be directed through the hollow core of the optical waveguide or the gas can be directed to the tissue through a tube separate from the hollow core. The radiation can be delivered from a laser (e.g., a $CO_2$ laser). The laser can have an output power of about 5 Watts or more (e.g., about 10 Watts or more, about 15 Watts or more, about 20 Watts or more, about 50 Watts or more, about 100 Watts or more). The radiation delivered to the tissue can have a power of about 1 Watt or more as measured at the distal end of the optical waveguide (e.g., about 2 Watts or more, 5 Watts or more, 8 Watts or more, 10 Watts or more, about 20 Watts or more, about 50 Watts or more). The radiation can have a wavelength of about 10.6 microns. The gas can have a flow rate of about 1 liter/min or more (e.g., about 2 liter/min or more, about 5 liter/min or more, about 8 liter/min or more, about 10 liter/min or more, about 12 liter/min or more, about 15 liter/min or more, about 20 liter/min or more).

The pressure of the gas exiting the hollow core can be relatively high. For example, the gas pressure exiting the fiber can correspond to a flow rate of about 1 liter/min or more (e.g., about 2 liter/min or more, about 5 liter/min or more, about 8 liter/min or more, about 10 liter/min or more, about 12 liter/min or more, about 15 liter/min or more, about 20 liter/min or more) through a 1 meter length of fiber having a core diameter of about 500 μm.

The gas can include air, nitrogen, oxygen, carbon dioxide or a noble gas (e.g., He, Ne, Ar, Kr, and/or Xe). The gas can include substantially only one compound (e.g., about 98% or more of one compound, about 99% or more, about 99.5% or more, about 99.8% or more, about 99.9% or more). Alternatively, in some embodiments, the gas can include a mixture of different compounds (e.g., air).

The method can further include excising tissue with the radiation. The optical waveguide can be a photonic crystal fiber (e.g., a Bragg fiber). The gas can have a temperature of about 50° C. or more at the tissue (e.g., about 60° C. or more, about 70° C. or more, about 80° C. or more, about 90° C. or more, about 100° C. or more). The method can further include bending the fiber while delivering radiation to the tissue. The fiber bend can have a radius of curvature of about 12 cm or less (e.g., about 10 cm or less, about 8 cm or less, about 7 cm or less, about 6 cm or less, about 5 cm or less, about 4 cm or less, about 3 cm or less, about 2 cm or less).

A number of references are incorporated herein by reference. In case of conflict, the present application will control.

The details of one or more embodiments of the invention are set forth in the accompanying drawings and the description below. Other features and advantages of the invention will be apparent from the description and drawings, and from the claims.

DESCRIPTION OF DRAWINGS

FIG. 1 is a schematic diagram of an embodiment of a laser medical system that includes a photonic crystal fiber.

FIG. 4A-4D are cross-sectional views of embodiments of sleeves attached to an output end of a photonic crystal fiber.

FIG. 8 is a schematic diagram of a portion of a medical laser system that includes a photonic crystal fiber and a second fiber waveguide.

FIG. 9 is a schematic diagram of a portion of a medical laser system that includes a photonic crystal fiber and a tube for exhausting fluid from the fiber.

Like reference symbols in the various drawings indicate like elements.

DETAILED DESCRIPTION

Figure 2A:
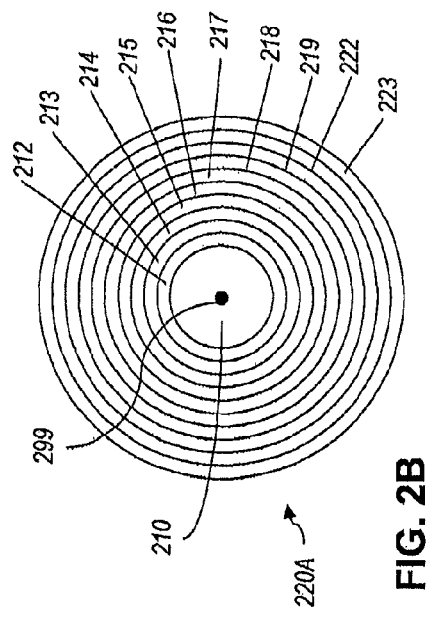
FIG. 2A is a cross-section view of an embodiment of a photonic crystal fiber.

Referring to FIG. 1, a medical laser system 100 includes a $CO_2$ laser 110, and a photonic crystal fiber 120 having a hollow core to guide radiation 112 from the laser to a target location 99 of a patient. Radiation 112 has a wavelength of 10.6 microns. Laser radiation 112 is coupled by a coupling assembly 130 into the hollow core of photonic crystal fiber 120, which delivers the radiation through a handpiece 140 to target location 99. During use, an operator (e.g., a medical practitioner, such as a surgeon, a dentist, an ophthalmologist, or a veterinarian) grips a portion 142 of handpiece 140, and manipulates the handpiece to direct laser radiation 113 emitted from an output end of photonic crystal fiber 120 to target location 99 in order to perform a therapeutic function at the target location. For example, the radiation can be used to excise, incise, ablate, or vaporize tissue at the target location.

$CO_2$ laser 110 is controlled by an electronic controller 150 for setting and displaying operating parameters of the system. The operator controls delivery of the laser radiation using a remote control 152, such as a foot pedal. In some embodiments, the remote control is a component of handpiece 140, allowing the operator to control the direction of emitted laser radiation and delivery of the laser radiation with one hand or both hands.

In addition to grip portion 142, handpiece 140 includes a stand off tip 144, which maintains a desired distance (e.g., from about 0.1 millimeters to about 30 millimeters) between the output end of fiber 120 and target tissue 99. The stand off tip assist the operator in positioning the output end of photonic crystal fiber 120 from target location 99, and can also reduce clogging of the output end due to debris at the target location. In some embodiments, handpiece 140 includes optical components (e.g., a lens or lenses), which focus the beam emitted from the fiber to a desired spot size. The waist of the focused beam can be located at or near the distal end of the stand off tip.

In some embodiments, fiber 120 can be easily installed and removed from coupling assembly 130, and from handpiece 140 (e.g., using conventional fiber optic connectors). This can facilitate ease of use of the system in single-use applications, where the fiber is replaced after each procedure.

Typically, $CO_2$ laser 110 has an average output power of about 5 Watts to about 80 Watts at 10.6 microns (e.g., about 10 Watts or more, about 20 Watts or more). In many applications, laser powers of about 5 Watts to about 30 Watts are sufficient for the system to perform its intended function. For example, where system 100 is being used to excise or incise tissue, the radiation is confined to a small spot size and a laser having an average output power in this range is sufficient.

In certain embodiments, however, laser 110 can have an output power as high as about 100 Watts or more (e.g., up to about 500 Watts). For example, in applications where system 100 is used to vaporize tissue over a relatively large area (e.g., several square millimeters or centimeters), extremely high power lasers may be desirable.

Photonic crystal fiber can deliver the radiation from laser 110 to the target location with relatively high efficiency. For example, the fiber average output power can be about 50% or more of the fiber input energy (e.g., about 60% or more, about 70% or more, about 80% or more). Accordingly, the fiber's output power can be about 3 Watts or more (e.g., about 8 Watts or more, about 10 Watts or more, about 15 Watts or more). In certain embodiments, however, the average output power from the fiber can be less than 50% of the laser power, and still be sufficiently high to perform the intended procedure. For example, in some embodiments, the fiber average output power can be from about 20% to about 50% of the laser average output power.

The length of photonic crystal fiber 120 can vary as desired. In some embodiments, the fiber is about 1.2 meters long or more (e.g., about 1.5 meters or more, about 2 meters or more, about 3 meters or more, about 5 meters or more). The length is typically dependent on the specific application for which the laser system is used. In applications where laser 110 can be positioned close to the patient, and/or where the range of motion of the handpiece desired for the application is relatively small, the length of the fiber can be relatively short (e.g., about 1.5 meters or less, about 1.2 meters or less, about 1 meter or less). In certain applications, the length of fiber 120 can be very short (e.g., about 50 centimeters or less, about 20 centimeters or less, about 10 centimeters or less). For example, very short lengths of photonic crystal fiber may be useful in procedures where the system can deliver radiation from the laser to the fiber by some other means (e.g., a different waveguide or an articulated arm). Very short fiber lengths may be useful for nose and ear procedures, for example.

However, in applications where it is inconvenient for the laser to be placed in close proximity to the patient and/or where a large range of motion of the handpiece is desired, the length of the fiber is longer (e.g., about 2 meters or more, about 5 meters or more, about 8 meters or more). For example, in surgical applications, where a large team of medical practitioners is needed in close proximity to the patient, it may be desirable to place the laser away from the operating table (e.g., in the corner of the operating room, or in a different room entirely). In such situations, a longer fiber may be desirable.

In general, photonic crystal fiber 120 is flexible, and can be bent to relatively small radii of curvature over relatively large angles without significantly impacting its performance (e.g., without causing the fiber to fail, or without reducing the fiber transmission to a level where the system cannot be used for its intended use while the fiber is bent). In some embodiments, an operator can bend photonic crystal fiber 120 to have a relatively small radius of curvature, such as about 15 cm or less (e.g., about 10 cm or less, about 8 cm or less, about 5 cm or less, about 3 cm or less) while still delivering sufficient power to the target location for the system to perform its function.

In general, the angle through which the fiber is bent can vary, and usually depends on the procedure being performed. For example, in some embodiments, the fiber can be bent through about 90° or more (e.g., about 120° or more, about 150° or more).

Losses of transmitted power due to the operator bending photonic crystal fiber 120 may be relatively small. In general, losses due to bends should not significantly damage the fiber, e.g., causing it to fail, or reduce the fiber output power to a level where the system can no longer perform the function for which it is designed. Embodiments of photonic crystal fiber 120 (e.g., about 1 meter or more in length) can be bent through 90° with a bend radius of about 5 centimeters or less, and still transmit about 30% or more (e.g., about 50% or more, about 70% or more) of radiation coupled into the fiber at the guided wavelength. These fibers can provide such transmission characteristics and provide average output power of about 3 Watts or more (e.g., about 5 Watts or more, about 8 Watts or more, about 10 Watts or more).

The quality of the beam of the laser radiation emitted from the output end of fiber 120 can be relatively good. For example, the beam can have a low $M^2$ value, such as about 4 or less (e.g., about 3 or less, about 2.5 or less, about 2 or less). $M^2$ is a parameter commonly used to describe laser beam quality, where an $M^2$ value of about 1 corresponds to a $TEM_{00}$ beam emitted from a laser, which has a perfect Gaussian profile. The $M^2$ value is related to the minimum spot size that can be formed from the beam according to the formula:

$$d_s = 1.27 f \lambda M^2 / d_b \quad (1)$$

where $d_s$ is the minimum spot diameter, $d_b$ is the beam diameter prior to being focused to the spot by a lens having focal length f. Accordingly, the minimum possible spot size a beam can be focused is proportional to the $M^2$ value for the beam. Practically, beams having smaller values of $M^2$ can provide higher radiation power densities to the target area, with less damage to surrounding tissue due to the decreased spot size.

The spot size of radiation delivered by photonic crystal fiber 120 to the target tissue can be relatively small. For example, in certain embodiments, the spot can have a diameter of about 500 microns or less (e.g., about 300 microns or less, about 200 microns or less, such as about 100 microns) at a desired working distance from the fiber's output end (e.g., from about 0.1 mm to about 3 mm). As discussed previously, a small spot size is desirable where system 100 is being used to excise or incise tissue or in other applications where substantial precision in the delivery of the radiation is desired. Alternatively, in applications where tissue is to be ablated or vaporized, and/or a lesser level of precision is sufficient, the spot size can be relatively large (e.g., having a diameter of about 2 millimeters or more, about 3 millimeters or more, about 4 millimeters or more).

While laser 110 is a $CO_2$ laser, photonic crystal fibers can be used in medical laser systems that use other types or lasers, operating at wavelengths different from 10.6 microns. In general, medical laser systems can provide radiation at ultraviolet (UV), visible, or infrared (IR) wavelengths. Lasers delivering IR radiation, for example, emit radiation having a wavelength between about 0.7 microns and about 20 microns (e.g., between about 2 to about 5 microns or between about 8 to about 12 microns). Waveguides having hollow cores, such as photonic crystal fiber 120, are well-suited for use with laser systems having wavelengths of about 2 microns or more, since gases that commonly occupy the core have relatively low absorptions at these wavelengths compared to many dielectric materials (e.g., silica-based glasses and various polymers). In addition to $CO_2$ lasers, other examples of lasers which can emit IR radiation include Nd:YAG lasers (e.g., at 1.064 microns), Er:YAG lasers (e.g., at 2.94 microns), Er, Cr:YSGG (Erbium, Chromium doped Yttrium Scandium Gallium Garnet) lasers (e.g., at 2.796 microns), Ho:YAG lasers (e.g., at 2.1 microns), free electron lasers (e.g., in the 6 to 7 micron range), and quantum cascade lasers (e.g., in the 3 to 5 micron range).

In general, the type of laser used in a medical laser system depends on the purpose for which the system is designed. The type of laser can be selected depending on whether the system is to be used in surgical procedures, in diagnosis, or in physiologic studies. For example, an argon laser, which delivers in the blue and green regions of the visible light spectrum, with two energy peaks, at 488 nm and 514 nm, can be used for photocoagulation. A dye laser, which is a laser with organic dye dissolved in a solvent as the active medium whose beam is in the visible light spectrum, can be used in photodynamic therapy. Excimer lasers provide radiation in the ultraviolet spectrum, penetrates tissues only a small distance, can be used to break chemical bonds of molecules in tissue instead of generating heat to destroy tissue. Such lasers can be used in ophthalmological procedures and laser angioplasty. Ho:YAG lasers can provide radiation in the near infrared spectrum and can be used for photocoagulation and photoablation. Krypton lasers provide radiation in the yellow-red visible light spectrum, and can be used for photocoagulation. Radiation from KTP lasers can be frequency-doubled to provide radiation in the green visible light spectrum and can be used for photoablation and photocoagulation. Nd:YAG lasers can be for photocoagulation and photoablation. Pulsed dye lasers can be used to provide in the yellow visible light spectrum (e.g., with a wavelength of 577 nm or 585 nm), with alternating on and off phases of a few microseconds each, and can be used to decolorize pigmented lesions.

In general, laser systems can use continuous wave or pulsed lasers. Furthermore, while $CO_2$ lasers are typically used at average output powers of about 5 Watts to about 100 Watts, photonic crystal fibers can generally be used with a variety of laser powers. For example, average laser power can be in the milliWatt range in certain systems, up to as much as several hundred Watts (e.g., about 200 Watts or more) in extremely high power systems.

In general, for high power systems, the average power density guided by fiber 120 can be extremely high. For example, power density in the fiber, or exiting the fiber's core, can be about $10^3$ W/cm$^2$ or more (e.g., about $10^4$ W/cm$^2$ or more, about $10^5$ W/cm$^2$ or more, $10^6$ W/cm$^2$ or more).

Referring to FIG. 2A, in general, photonic crystal fiber 120 includes a core 210, which is surrounded by a confinement region 220 extending along a waveguide axis 299 (normal to the plane of FIG. 2A). Confinement region 220 is surrounded by a cladding 230 (e.g., a polymer cladding), which provides mechanical support and protects the core and confinement region from environmental hazards. Confinement region 220 includes a photonic crystal structure that substantially confines radiation at a wavelength λ to core 210. Examples of such structures are described with reference to FIGS. 2B-2D below. As used herein, a photonic crystal is a structure (e.g., a dielectric structure) with a refractive index modulation (e.g., a periodic refractive index modulation) that produces a photonic bandgap in the photonic crystal. An example of such a structure, giving rise to a one dimensional refractive index modulation, is a stack of dielectric layers of high and low refractive index, where the layers have substantially the same optical thickness. A photonic bandgap, as used herein, is a range of frequencies in which there are no accessible extended (i.e., propagating, non-localized) states in the dielectric structure. Typically the structure is a periodic dielectric structure, but it may also include, e.g., more complex "quasi-crystals." The bandgap can be used to confine, guide, and/or localize light by combining the photonic crystal with "defect" regions that deviate from the bandgap structure. Moreover, there are accessible extended states for frequencies both below and above the gap, allowing light to be confined even in lower-index regions (in contrast to index-guided TIR structures). The term "accessible" states means those states with which coupling is not already forbidden by some symmetry or conservation law of the system. For example, in two-dimensional systems, polarization is conserved, so only states of a similar polarization need to be excluded from the bandgap. In a waveguide with uniform cross-section (such as a typical fiber), the wavevector β is conserved, so only states with a given β need to be excluded from the bandgap to support photonic crystal guided modes. Moreover, in a waveguide with cylindrical symmetry, the "angular momentum" index m is conserved, so only modes with the same m need to be excluded from the bandgap. In short, for high-symmetry systems the requirements for photonic bandgaps are considerably relaxed compared to "complete" bandgaps in which all states, regardless of symmetry, are excluded.

Theoretically, a photonic crystal is only completely reflective in the bandgap when the index modulation in the photonic crystal has an infinite extent. Otherwise, incident radiation can "tunnel" through the photonic crystal via an evanescent mode that couples propagating modes on either side of the photonic crystal. In practice, however, the rate of such tunneling decreases exponentially with photonic crystal thickness (e.g., the number of alternating layers). It also decreases with the magnitude of the index contrast in the confinement region.

Furthermore, a photonic bandgap may extend over only a relatively small region of propagation vectors. For example, a dielectric stack may be highly reflective for a normally incident ray and yet only partially reflective for an obliquely incident ray. A "complete photonic bandgap" is a bandgap that extends over all possible wavevectors and all polarizations. Generally, a complete photonic bandgap is only associated with a photonic crystal having index modulations along three dimensions. However, in the context of EM radiation incident on a photonic crystal from an adjacent dielectric material, we can also define an "omnidirectional photonic bandgap," which is a photonic bandgap for all possible wavevectors and polarizations for which the adjacent dielectric material supports propagating EM modes. Equivalently, an omnidirectional photonic bandgap can be defined as a photonic band gap for all EM modes above the light line, wherein the light line defines the lowest frequency propagating mode supported by the material adjacent the photonic crystal. For example, in air the light line is approximately given by ω=cβ, where ω is the angular frequency of the radiation, β is the wavevector, and c is the speed of light. A description of an omnidirectional planar reflector is disclosed in U.S. Pat. No. 6,130,780, the entire contents of which are incorporated herein by reference. Furthermore, the use of alternating dielectric layers to provide omnidirectional reflection (in a planar limit) for a cylindrical waveguide geometry is disclosed in Published PCT application WO 00/22466, the contents of which are incorporated herein by reference.

When confinement region 220 gives rise to an omnidirectional bandgap with respect to core 210, the guided modes are strongly confined because, in principle, any EM radiation incident on the confinement region from the core is completely reflected. As described above, however, such complete reflection only occurs when there are an infinite number of layers. For a finite number of layers (e.g., about 20 layers), an omnidirectional photonic bandgap may correspond to a reflectivity in a planar geometry of at least 95% for all angles of incidence ranging from 0° to 80° and for all polarizations of EM radiation having frequency in the omnidirectional bandgap. Furthermore, even when fiber 120 has a confinement region with a bandgap that is not omnidirectional, it may still support a strongly guided mode, e.g., a mode with radiation losses of less than 0.1 dB/km for a range of frequencies in the bandgap. Generally, whether or not the bandgap is omnidirectional will depend on the size of the bandgap produced by the alternating layer (which generally scales with index contrast of the two layers) and the lowest-index constituent of the photonic crystal.

Regarding the structure of photonic crystal fiber 120, in general, the diameter of core 210 (indicated by reference numeral 211 in FIG. 2A) can vary depending on the end-use application of system 100. For example, where a large spot size is desired, the core can be relatively large (e.g., about 1 mm or more, about 2 mm or more). Alternatively, when a small spot size is desired, core diameter 211 can be much smaller (e.g., about 500 microns or less, about 300 microns or less, about 200 microns or less, about 100 microns or less).

More generally, where fiber 120 is used in systems with other types of laser, and/or used to guide wavelengths other than 10.6 microns, the core diameter depends on the wavelength or wavelength range of the energy to be guided by the fiber, and on whether the fiber is a single or multimode fiber. For example, where the fiber is a single mode fiber for guiding visible wavelengths (e.g., between about 400 nm and about 800 nm) the core radius can be in the sub-micron to several micron range (e.g., from about 0.5 microns to about 5 microns). However, the core radius can be in the tens to thousands of microns range (e.g., from about 10 microns to about 2,000 microns, such as about 500 microns to about 1,000 microns), for example, where the fiber is a multimode fiber for guiding IR wavelengths. The core radius can be about 5λ or more (e.g., about 10λ or more, about 20λ or more, about 50λ or more, about 100λ or more), where λ is the wavelength of the guided energy.

An advantage of photonic crystal fibers is that fibers having small core diameters can be readily produced since fibers can be drawn from a perform, preserving the relative proportions of the fiber's cross-sectional structure while reducing the dimensions of that structure to small sizes in a controlled manner.

In photonic crystal fiber 120, core 220 is hollow. Alternatively, in embodiments where there are no fluids pumped through the core, core 220 can include any material or combination of materials that are rheologically compatible with the materials forming confinement region 220 and that have sufficiently high transmission properties at the guided wavelength(s). In some embodiments, core 220 includes a dielectric material (e.g., an amorphous dielectric material), such as an inorganic glass or a polymer. In certain embodiments, core 220 can include one or more dopant materials, such as those described in U.S. patent application Ser. No. 10/121,452, entitled "HIGH INDEX-CONTRAST FIBER WAVEGUIDES AND APPLICATIONS," filed Apr. 12, 2002 and now published under Pub. No. US-2003-0044158-A1, the entire contents of which are hereby incorporated by reference.

Cladding 230 can be formed from a polymer (e.g., an acrylate or silicone polymer) or other material. Cladding 230 can be formed from a material that is also used to as part of confinement region 220, which are described below. In applications where the cladding comes in contact with a patient, it can be formed from materials that conform to FDA standards for medical devices. In these instances, silicone polymers, for example, may be particularly suited for use as the cladding material. Typically, cladding 230 protects the fiber from external damage. By selecting the appropriate thickness, composition, and/or structure, cladding 230 can also be designed to limit the flexibility of the fiber, e.g., to prevent damage by small radius of curvature bends.

In general, the thickness of fiber 120 can vary. The thickness is indicated by outer diameter (OD) 231 in FIG. 2A. OD 231 can be selected so that fiber 120 is compatible with other pieces of equipment. For example, fiber 120 can be made so that OD 231 is sufficiently small so that the fiber can be threaded through a channel in an endoscope or other tool (e.g., OD 231 can be about 2,000 microns or less). In some embodiments, fiber 120 has a relatively small OD (e.g., about 1,000 microns or less). Narrow fibers can be useful in applications where they are to be inserted into narrow spaces, such as through a patient's urethra. Alternatively, in some embodiments, diameter 231 can be relatively large compared (e.g., about 3,000 microns or more). Large OD's can reduce the mechanical flexibility of the fiber, which can prevent the fiber from bending to small radii of curvature that damage the fiber or reduce its transmission to a level where the system can no longer perform its intended function.

In addition to cladding 230, fiber 200 may include additional components to limit bend radii. For example, the fiber may include a spirally wound material around its outer diameter (e.g., a spirally wound wire). Alternatively, or additionally, the fiber may include additional claddings to provide additional mechanical support.

Although the fiber can be bent (as discussed above), in some embodiments, the fiber may be constrained from bending to radii of curvature of less than about 20 cm (e.g., about 10 cm or less, 8 cm or less, 5 cm or less) during regular use in the application for which it is designed.

The cladding material may be selected so that the fiber is sterilizable. For example, the cladding material may be selected so that the fiber can withstand high temperatures (e.g., those experienced in an autoclave).

Figure 2B:
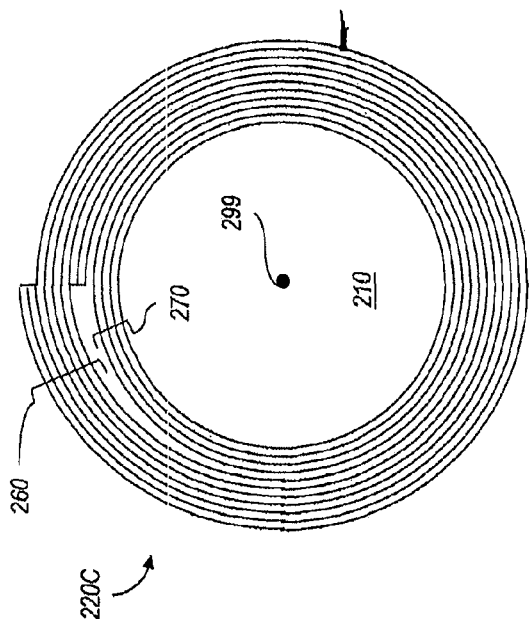
FIG. 2B-2D are cross-sectional views of embodiments of confinement regions for photonic crystal fibers.

Turning to the structure and composition of confinement region 220, in some embodiments, photonic crystal fiber 120 is a Bragg fiber and confinement region 220 includes multiple alternating layers having high and low refractive indexes, where the high and low index layers have similar optical thickness. For example, referring to FIG. 2B, in some embodiments, confinement region 220A includes multiple annular dielectric layers of differing refractive index (i.e., layers composed of a high index material having a refractive index $n_H$, and layers composed of a low index material having a refractive index $n_L$), indicated as layers 212, 213, 214, 215, 216, 217, 218, 219, 222, and 223. Here, $n_H > n_L$ and $n_H - n_L$ can be, for example, about 0.01 or more, about 0.05 or more, about 0.1 or more, about 0.2 or more, about 0.5 or more. For convenience, only a few of the dielectric confinement layers are shown in FIG. 2B. In practice, confinement region 220A may include many more layers (e.g., about 15 layers or more, about 20 layers or more, about 30 layers or more, about 40 layers or more, about 50 layers or more, about 80 layers or more).

In some embodiments, confinement region 220 can give rise to an omnidirectional bandgap with respect to core 210, wherein the guided modes are strongly confined because, in principle, any EM radiation incident on the confinement region from the core is completely reflected. However, such complete reflection only occurs when there are an infinite number of layers. For a finite number of layers (e.g., about 20 layers), an omnidirectional photonic bandgap may correspond to a reflectivity in a planar geometry of at least 95% for all angles of incidence ranging from 0° to 80° and for all polarizations of EM radiation having frequency in the omnidirectional bandgap. Furthermore, even when fiber 120 has a confinement region with a bandgap that is not omnidirectional, it may still support a strongly guided mode, e.g., a mode with radiation losses of less than 0.1 dB/km for a range of frequencies in the bandgap. Generally, whether or not the bandgap is omnidirectional will depend on the size of the bandgap produced by the alternating layers (which generally scales with index contrast of the two layers) and the lowest-index constituent of the photonic crystal.

The existence of an omnidirectional bandgap, however, may not be necessary for useful application of fiber 120. For example, in some embodiments, a laser beam used to establish the propagating field in the fiber is a $TEM_{00}$ mode. This mode can couple with high efficiency to the $HE_{11}$ mode of a suitably designed fiber. Thus, for successful application of the fiber for transmission of laser energy, it may only be necessary that the loss of this one mode be sufficiently low. More generally, it may be sufficient that the fiber support only a number of low loss modes (e.g., the $HE_{11}$ mode and the modes that couple to it from simple perturbations, such as bending of the fiber). In other words, photonic bandgap fibers may be designed to minimize the losses of one or a group of modes in the fiber, without necessarily possessing an omnidirectional bandgap.

For a planar dielectric reflector, it is well-known that, for normal incidence, a maximum band gap is obtained for a "quarter-wave" stack in which each layer has equal optical thickness λ/4, or equivalently $n_{hi}d_{hi}=n_{lo}d_{lo}=\lambda/4$, where $d_{hi/lo}$ and $n_{hi/lo}$ refer to the thickness and refractive index, respectively, of high-index and low-index layers in the stack. Normal incidence, however, corresponds to β=0, whereas for a cylindrical waveguide the desired modes typically lie near the light line ω=cβ (in the limit of large R, the lowest-order modes are essentially plane waves propagating along z-axis, i.e., the waveguide axis). In this case, the quarter-wave condition becomes:

$$d_{hi}\sqrt{n_{hi}^2-1}=d_{lo}\sqrt{n_{lo}^2-1}=\lambda/4 \qquad (2)$$

This equation may not be exactly optimal because the quarter-wave condition is modified by the cylindrical geometry, which may require the optical thickness of each layer to vary smoothly with its radial coordinate. In addition, the differing absorption of the high and low index materials can change the optimal layer thicknesses from their quarter-wave values.

In certain embodiments, confinement region 220 includes layers that do not satisfy the quarter-wave condition given in Eq. 2. In other words, for the example shown in FIG. 2B, one or more of layers 212, 213, 214, 215, 216, 217, 218, 219, 222, and 223 are thicker or thinner than $d_{\lambda/4}$, where $$d_{\lambda/4} = \frac{\lambda}{4\sqrt{n^2-1}},$$

and n is the refractive index of the layer (i.e., $d_{\lambda/4}$ corresponds to an optical thickness equal to the quarter-wave thickness). For example, one or more layers in the confinement region can have a thickness of about 0.9 $d_{\lambda/4}$ or less (e.g., about 0.8 $d_{\lambda/4}$ or less, about 0.7 $d_{\lambda/4}$ or less, about 0.6 $d_{\lambda/4}$ or less, about 0.5 $d_{\lambda/4}$ or less, about 0.4 $d_{\lambda/4}$ or less, about 0.3 $d_{\lambda/4}$ or less), or about 1.1 $d_{\lambda/4}$ or more (e.g., about 1.2 $d_{\lambda/4}$ or more, about 1.3 $d_{\lambda/4}$ or more, about 1.4 $d_{\lambda/4}$ or more, about 1.5 $d_{\lambda/4}$ or more, about 1.8 $d_{\lambda/4}$ or more, about 2.0 $d_{\lambda/4}$ or more). In some embodiments, all layers in the confinement region can be detuned from the quarter-wave condition. In some embodiments, the thickness of one or more of the high index layers can be different (e.g., thicker or thinner) from the thickness of the other high index layers. For example, the thickness of the innermost high index layer can be different from the thickness of the other high index layers. Alternatively, or additionally, the thickness of one or more of the low index layers can be different (e.g., thicker or thinner) from the thickness of the other low index layers. For example, the thickness of the innermost low index layer can be different from the thickness of the other low index layers.

Detuning the thickness of layers in the confinement region from the quarter-wave condition can reduce the attenuation of photonic crystal fiber 120 compared to a test fiber, which refers to a fiber identical to photonic crystal fiber 120, except that the quarter-wave condition is satisfied for all layers in the confinement region (i.e., the test fiber has an identical core, and its confinement region has the same number of layers with the same composition as photonic crystal fiber 120). For example, fiber 120 can have an attenuation for one or more guided modes that is reduced by a factor of about two or more compared to the attenuation of the test fiber (e.g., reduced by a factor of about three or more, about four or more, about five or more, about ten or more, about 20 or more, about 50 or more, about 100 or more). Examples of photonic crystal fibers illustrating reduce attenuation are described in U.S. patent application Ser. No. 10/978,605, entitled "PHOTONIC CRYSTAL WAVEGUIDES AND SYSTEMS USING SUCH WAVEGUIDES," filed on Nov. 1, 2004, the entire contents of which is hereby incorporated by reference.

The thickness of each layer in the confinement region can vary depending on the composition and structure of the photonic crystal fiber. Thickness can also vary depending on the wavelength, mode, or group of modes for which the photonic crystal fiber is optimized. The thickness of each layer can be determined using theoretical and/or empirical methods. Theoretical methods include computational modeling. One computational approach is to determine the attenuation of a fiber for different layer thicknesses and use an optimization routine (e.g., a non-linear optimization routine) to determine the values of layer thickness that minimize the fiber's attenuation for a guided mode. For example, the "downhill simplex method", described in the text *Numerical Recipes in FORTRAN* (*second editions*), by W. Press, S. Teukolsky, W. Vetterling, and B Flannery, can be used to perform the optimization.

Such a model should account for different attenuation mechanisms in a fiber. Two mechanisms by which energy can be lost from a guided EM mode are by absorption loss and radiation loss. Absorption loss refers to loss due to material absorption. Radiation loss refers to energy that leaks from the fiber due to imperfect confinement. Both modes of loss contribute to fiber attenuation and can be studied theoretically, for example, using transfer matrix methods and perturbation theory. A discussion of transfer matrix methods can be found in an article by P. Yeh et al., *J. Opt. Soc. Am.*, 68, p. 1196 (1978). A discussion of perturbation theory can found in an article by M. Skorobogatiy et al., *Optics Express*, 10, p. 1227 (2002). Particularly, the transfer matrix code finds propagation constants β for the "leaky" modes resonant in a photonic crystal fiber structure. Imaginary parts of β's define the modal radiation loss, thus $Loss_{radiation} \sim Im(\beta)$. Loss due to material absorption is calculated using perturbation theory expansions, and in terms of the modal field overlap integral it can be determined from $$Loss_{absorption} \sim 2\pi\omega \int_0^\infty r\,dr(\alpha\vec{E}_\beta^*\vec{E}_\beta), \qquad (3)$$

where ω is the radiation frequency, r is the fiber radius, α is bulk absorption of the material, and $\vec{E}_\beta$ is an electric field vector.

Alternatively, the desired mode fields that can propagate in the fiber can be expanded in a suitable set of functions, such as B-splines (see, e.g., *A Practical Guide to Splines*, by C. deBoor). Application of the Galerkin conditions (see, e.g., Computational Galerkin Methods, C. A. J. Fletcher, Springer-Verlag, 1984) then converts Maxwell's equations into a standard eigenvalue-eigenvector problem, which can be solved using the LAPACK software package (freely available, for example, from the netlib repository on the interne, at "http://www.netlib.org"). The desired complex propagation constants, containing both material and radiation losses, are obtained directly from the eigenvalues.

Guided modes can be classified as one of three types: pure transverse electric (TE); pure transverse magnetic (TM); and mixed modes. Loss often depends on the type of mode. For example, TE modes can exhibit lower radiation and absorption losses than TM/mixed modes. Accordingly, the fiber can be optimized for guiding a mode that experiences low radiation and/or absorption loss.

While confinement region 220A includes multiple annular layers that give rise to a radial refractive index modulation, in general, confinement regions can also include other structures to provide confinement properties. For example, referring to FIG. 2C, a confinement region 220B includes continuous layers 240 and 250 of dielectric material (e.g., polymer, glass) having different refractive indices, as opposed to multiple discrete, concentric layers. Continuous layers 240 and 250 form a spiral around axis 299. One or more of the layers, e.g., layer 240 is a high-index layer having an index $n_H$ and a thickness $d_H$, and the layer, e.g., layer 250, is a low-index layer having an index $n_L$ and a thickness $d_L$, where $n_H > n_L$, (e.g., $n_H - n_L$ can be about 0.01 or more, about 0.05 or more, about 0.1 or more, about 0.2 or more, about 0.5 or more).

Because layers 240 and 250 spiral around axis 199, a radial section extending from axis 199 intersects each of the layers more than once, providing a radial profile that includes alternating high index and low index layers.

The spiraled layers in confinement region 220B provide a periodic variation in the index of refraction along a radial section, with a period corresponding to the optical thickness of layers 240 and 250. In general, the radial periodic variation has an optical period corresponding to $n_{240}d_{240} + n_{250}d_{250}$.

The thickness ($d_{240}$ and $d_{250}$) and optical thickness ($n_{240}d_{240}$ and $n_{250}d_{250}$) of layers 240 and 250 are selected based on the same considerations as discussed for confinement region 220A above.

Figure 2C:
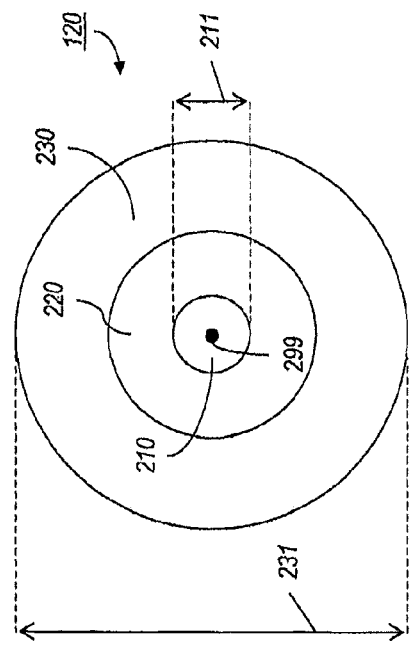

For the embodiment shown in FIG. 2C, confinement region 220B is 5 optical periods thick. In practice, however, spiral confinement regions may include many more optical periods (e.g., about 8 optical periods or more, about 10 optical periods or more, about 15 optical periods or more, about 20 optical periods or more, about 25 optical periods or more, such as about 40 or more optical periods).

Fiber's having spiral confinement regions can be formed from a spiral perform by rolling a planar multilayer film into a spiral and consolidating the spiral by fusing (e.g., by heating) the adjacent layers of the spiral together. In some embodiments, the planar multilayer film can be rolled into a spiral around a mandrel (e.g., a glass cylinder or rod), and the mandrel can be removed (e.g., by etching or by separating the mandrel from the spiral sheath and slipping it out of the sheath) after consolidation to provide the spiral cylinder. The mandrel can be formed from a single material, or can include portions of different materials. For example, in some embodiments, the mandrel can be coated with one or more layers that are not removed after consolidation of the rolled spiral structure. As an example, a mandrel can be formed from a first material (e.g., a silicate glass) in the form of a hollow rod, and a second material (e.g., another glass, such as a chalcogenide glass) coated onto the outside of the hollow rod. The second material can be the same as one of the materials used to form the multilayer film. After consolidation, the first material is etched, and the second material forms part of the fiber preform.

In some embodiments, additional material cart be disposed on the outside of the wrapped multilayer film. For example, a polymer film can be wrapped around the outside of the spiral, and subsequently fused to the spiral to provide an annular polymer layer (e.g., the cladding). In certain embodiments, both the multilayer film and an additional film can be wrapped around the mandrel and consolidated in a single fusing step. In embodiments, the multilayer film can be wrapped and consolidated around the mandrel, and then the additional film can be wrapped around the fused spiral and consolidated in a second fusing step. The second consolidation can occur prior to or after etching the mandrel. Optionally, one or more additional layers can be deposited (e.g., using CVD) within the spiral prior to wrapping with the additional film.

Methods for preparing spiral articles are described in U.S. Patent Application Ser. No. 10/733,873, entitled "FIBER WAVEGUIJES AND METHODS OF MAKING SAME," filed on Dec. 10, 2003, the entire contents of which are hereby incorporated by reference.

Figure 2D:
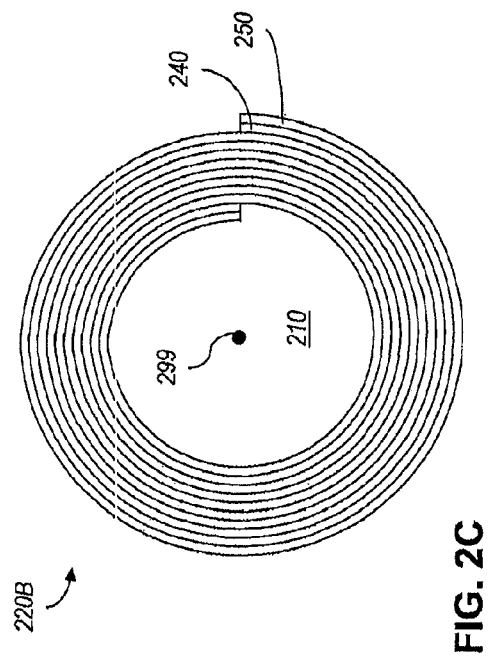

Referring to FIG. 2D, in some embodiments, photonic crystal fiber 120 can include a confinement region 220C that includes a spiral portion 260 and an annular portion 270. The number of layers in annular portion 270 and spiral portion 260 (along a radial direction from the fiber axis) can vary as desired. In some embodiments, annular portion can include a single layer. Alternatively, as shown in FIG. 2D, annular portion 270 can include multiple layers (e.g., two or more layers, three or more layers, four or more layers, five or more layers, ten or more layers).

In embodiments where annular portion 270 includes more than one layer, the optical thickness of each layer may be the same or different as other layers in the annular portion. In some embodiments, one or more of the layers in annular portion 270 may have an optical thickness corresponding to the quarter wave thickness (i.e., as given by Eq. (2). Alternatively, or additionally, one or more layers of annular portion 270 can have a thickness different from the quarter wave thickness. Layer thickness can be optimized to reduce (e.g., minimize) attenuation of guided radiation using the optimization methods disclosed herein.

In certain embodiments, annular portion 270 can be formed from materials that have relatively low concentrations of defects that would scatter and/or absorb radiation guided by photonic crystal fiber 120. For example, annular portion 270 can include one or more glasses with relatively low concentrations of inhomogeneities and/or impurities. Inhomogeneities and impurities can be identified using optical or electron microscopy, for example. Raman spectroscopy, glow discharge mass spectroscopy, sputtered neutrals mass spectroscopy or Fourier Transform Infrared spectroscopy (FTIR) can also be used to monitor inhomogeneities and/or impurities in photonic crystal fibers.

In certain embodiments, annular portion 270 is formed from materials with a lower concentration of defects than spiral portion 260. In general, these defects include both structural defects (e.g., delamination between layers, cracks) and material inhomogeneities (e.g., variations in chemical composition and/or crystalline structure).

Fibers having confinement regions such as shown in FIG. 2D can be prepared by depositing one or more annular layers onto a surface of a cylinder having a spiral cross-section to form a preform. The photonic crystal fiber can then be drawn from the preform.

Annular layers can be deposited onto a surface of the spiral cylinder using a variety of deposition methods. For example, where the spiral portion is between the annular portion and the core, material can be evaporated or sputtered onto the outer surface of the spiral article to form the preform.

In embodiments where the annular portion of the photonic crystal fiber is between the spiral portion and the core, material can be deposited on the inner surface of the spiral article by, for example, chemical vapor deposition (e.g., plasma enhanced chemical vapor deposition). Methods for depositing layers of, for example, one or more glasses onto an inner surface of a cylindrical preform are described in U.S. patent application Ser. No. 10/720,453, entitled "DIELECTRIC WAVEGUIDE AND METHOD OF MAKING THE SAME," filed on Nov. 24, 2003, the entire contents of which are hereby incorporated by reference.

In general, a confinement region may include photonic crystal structures different from a multilayer configuration.

For example, confinement region 220C includes both a spiral portion and annular portion, in some embodiments, confinement regions can include portions with other non-spiral structure. For example, a confinement region can include a spiral portion and a holey portion (e.g., composed of a solid cylinder perforated by a number of holes that extend along the fiber's axis). The holes can be arranged along concentric circles, providing a variation in the radial refractive index of the holey portion of the confinement region.

With regard to the composition of confinement region 220, the composition of high index and low index layers are typically selected to provide a desired refractive index contrast between the layers at the fiber's operational wavelength(s). The composition of each high index layer can be the same or different as other high index layers, just as the composition of each low index layer can be the same or different as other low index layers.

Suitable materials for high and low index layers can include inorganic materials such as inorganic glasses or amorphous alloys. Examples of inorganic glasses include oxide glasses (e.g., heavy metal oxide glasses), halide glasses and/or chalcogenide glasses, and organic materials, such as polymers. Examples of polymers include acrylonitrile-butadiene-styrene (ABS), poly methylmethacrylate (PMMA), cellulose acetate butyrate (CAB), polycarbonates (PC), polystyrenes (PS) (including, e.g., copolymers styrene-butadiene (SBC), methylestyrene-acrylonitrile, styrene-xylylene, styrene-ethylene, styrene-propylene, styrene-acylonitrile (SAN)), polyetherimide (PEI), polyvinyl acetate (PVAC), polyvinyl alcohol (PVA), polyvinyl chloride (PVC), polyoxymethylene; polyformaldehyde (polyacetal) (POM), ethylene vinyl acetate copolymer (EVAC), polyamide (PA), polyethylene terephthalate (PETP), fluoropolymers (including, e.g., polytetrafluoroethylene (PTFE), polyperfluoroalkoxythylene (PFA), fluorinated ethylene propylene (FEP)), polybutylene terephthalate (PBTP), low density polyethylene (PE), polypropylene (PP), poly methyl pentenes (PMP) (and other polyolefins, including cyclic polyolefins), polytetrafluoroethylene (PTFE), polysulfides (including, e.g., polyphenylene sulfide (PPS)), and polysulfones (including, e.g., polysulfone (PSU), polyehtersulfone (PES), polyphenylsulphone (PPSU), polyarylalkylsulfone, and polysulfonates). Polymers can be homopolymers or copolymers (e.g., (Co)poly(acrylamide-acrylonitrile) and/or acrylonitrile styrene copolymers). Polymers can include polymer blends, such as blends of polyamides-polyolefins, polyamides-polycarbonates, and/or PES-polyolefins, for example.

Further examples of polymers that can be used include cyclic olefin polymers (COPs) and cyclic olefin copolymers (COCs). In some embodiments, COPs and COCs can be prepared by polymerizing norbornen monomers or copolymerization norbornen monomers and other polyolefins (polyethylene, polypropylene). Commercially-available COPs and/or COCs can be used, including, for example, Zeonex® polymers (e.g., Zeonex® E48R) and Zeonor® copolymers (e.g., Zeonor® 1600), both available from Zeon Chemicals L.P. (Louisville, Ky.). COCs can also be obtained from Promerus LLC (Brecksville, Ohio) (e.g., such as FS1700).

Alternatively, or additionally, low-index regions may be fabricated by using hollow structural support materials, such as silica spheres or hollow fibers, to separate high-index layers or regions. Examples of fibers that include such structural supports are described in Published International Application WO 03/058308, entitled "BIREFRINGENT OPTICAL FIBRES," the entire contents of which are hereby incorporated by reference.

In certain embodiments, the confinement region is a dielectric confinement region, being composed of substantially all dielectric materials, such as one or more glasses and/or one or more dielectric polymers. Generally, a dielectric confinement region includes substantially no metal layers.

In some embodiments, the high index layers or low index layers of the confinement region can include chalcogenide glasses (e.g., glasses containing a chalcogen element, such as sulphur, selenium, and/or tellurium). In addition to a chalcogen element, chalcogenide glasses may include one or more of the following elements: boron, aluminum, silicon, phosphorus, sulfur, gallium, germanium, arsenic, indium, tin, antimony, thallium, lead, bismuth, cadmium, lanthanum and the halides (fluorine, chlorine, bromide, iodine).

Chalcogenide glasses can be binary or ternary glasses, e.g., As—S, As—Se, Ge—S, Ge—Se, As—Te, Sb—Se, As—S—Se, S—Se—Te, As—Se—Te, As—S—Te, Ge—S—Te, Ge—Se—Te, Ge—S—Se, As—Ge—Se, As—Ge—Te, As—Se—Pb, As—S—Tl, As—Se—Tl, As—Te—Tl, As—Se—Ga, Ga—La—S, Ge—Sb—Se or complex, multi-component glasses based on these elements such as As—Ga—Ge—S, Pb—Ga—Ge—S, etc. The ratio of each element in a chalcogenide glass can be varied.

In certain embodiments, in addition or alternative to chalcogenide glass(es), one or more layers in confinement region 220 can include one or more oxide glasses (e.g., heavy metal oxide glasses), halide glasses, amorphous alloys, or combinations thereof.

In general, the absorption of the high and low index layers varies depending on their composition and on the fiber's operational wavelength(s). In some embodiments, the material forming both the high and low index layers can have low absorption. A low absorption material has absorption of about 100 dB/m or less at the wavelength of operation (e.g., about 20 dB/m or less, about 10 dB/m or less, about 5 dB/m or less, about 1 dB/m or less, 0.1 dB/m or less). Examples of low absorption materials include chalcogenide glasses, which, at wavelengths of about 3 microns, exhibit an absorption coefficient of about 4 dB/m. At wavelengths of about 10.6 microns, chalcogenide glasses exhibit an absorption coefficient of about 10 dB/m. As another example, oxide glasses (e.g., lead borosilicate glasses, or silica) can have low absorption for wavelengths between about 1 and 2 microns. Some oxide glasses can have an absorption coefficient of about 1 dB/m to 0.0002 dB/m in this wavelength range.

Alternatively, one or both of the high and low index materials can have high absorption (e.g., about 100 dB/m or more, such as about 1,000 or more, about 10,000 or more, about 20,000 or more, about 50,000 dB/m or more). For example, many polymers exhibit an absorption coefficient of about $10^5$ dB/m for wavelengths between about 3 and about 11 microns. Examples of such polymers include polyetherimide (PEI), polychlorotrifluoro ethylene (PCTFE), perfluoroalkoxyethylene (PFA), and polyethylene naphthalate (PEN). PEI has an absorption of more than about $10^5$ dB/m at 3 microns, while PCTFE, PFA, and PEN have absorptions of more than about $10^5$ dB/m at 10.6 microns.

In some embodiments, the high index material has a low absorption coefficient and the low absorption material has a high absorption coefficient, or vice versa.

A material's absorption can be determined by measuring the relative transmission through at least two different thicknesses, $T_1$ and $T_2$, of the material. Assuming the field in the material decays with thickness T according to $Pe^{-\alpha T}$, with P representing the power incident on the material, the measured transmitted power through thicknesses $T_1$ and $T_2$ will then be $P_1 = Pe^{-\alpha T_1}$ and $P_2 = Pe^{-\alpha T_2}$. The absorption coefficient $\alpha$ is then obtained as $$\alpha = -\frac{1}{T_2 - T_1} \ln(P_2/P_1).$$

If desired, a more accurate evaluation of α can be obtained by using several thicknesses and performing a least squares fit to the logarithm of the transmitted power.

As discussed previously, materials can be selected for the confinement region to provide advantageous optical properties (e.g., low absorption with appropriate indices of refraction at the guided wavelength(s)). However, the materials should also be compatible with the processes used to manufacture the fiber. In some embodiments, the high and low index materials should preferably be compatible for co-drawing. Criteria for co-drawing compatibility are provided in aforementioned U.S. patent application Ser. No. 10/121,452, entitled "HIGH INDEX-CONTRAST FIBER WAVEGUIDES AND APPLICATIONS." In addition, the high and low index materials should preferably be sufficiently stable with respect to crystallization, phase separation, chemical attack and unwanted reactions for the conditions (e.g., environmental conditions such as temperature, humidity, and ambient gas environment) under which the fiber is formed, deployed, and used.

When making a robust fiber waveguides using a drawing process, not every combination of materials with desired optical properties is necessarily suitable. Typically, one should select materials that are rheologically, thermo-mechanically, and physico-chemically compatible. Several criteria for selecting compatible materials will now be discussed.

A first criterion is to select materials that are rheologically compatible. In other words, one should select materials that have similar viscosities over a broad temperature range, corresponding to the temperatures experience during the different stages of fiber drawing and operation. Viscosity is the resistance of a fluid to flow under an applied shear stress. Here, viscosities are quoted in units of Poise. Before elaborating on rheological compatibility, it is useful define a set of characteristic temperatures for a given material, which are temperatures at which the given material has a specific viscosity.

The annealing point, $T_a$, is the temperature at which a material has a viscosity $10^{13}$ Poise. $T_a$ can be measured using a Model SP-2A System from Orton Ceramic Foundation (Westerville, Ohio). Typically, $T_a$ is the temperature at which the viscosity of a piece of glass is low enough to allow for relief of residual stresses.

The softening point, $T_s$, is the temperature at which a material has a viscosity $10^{7.65}$ Poise. $T_s$ can be measured using a softening point instrument, e.g., Model SP-3A from Orton Ceramic Foundation (Westerville, Ohio). The softening point is related to the temperature at which the materials flow changes from plastic to viscous in nature.

The working point, $T_w$, is the temperature at which a material has a viscosity $10^4$ Poise. $T_w$ can be measured using a glass viscometer, Model SP-4A from Orton Ceramic Foundation (Westerville, Ohio). The working point is related to the temperature at which a glass can be easily drawn into a fiber. In some embodiments, for example, where the material is an inorganic glass, the material's working point temperature can be greater than 250° C., such as about 300° C., 400° C., 500° C. or more.

The melting point, $T_m$, is the temperature at which a material has a viscosity $10^2$ Poise. $T_m$ can also be measured using a glass viscometer, e.g., Model SP-4A from Orton Ceramic Foundation (Westerville, Ohio). The melting point is related to the temperature at which a glass becomes a liquid and control of the fiber drawing process with respect to geometrical maintenance of the fiber becomes very difficult.

To be rheologically compatible, two materials should have similar viscosities over a broad temperature range, e.g., from the temperature at which the fiber is drawn down to the temperature at which the fiber can no longer release stress at a discernible rates (e.g., at $T_a$) or lower. Accordingly, the working temperature of two compatible materials should be similar, so that the two materials flow at similar rates when drawn. For example, if one measures the viscosity of the first material, $\eta_1(T)$ at the working temperature of the second material, $T_{w2}$, $\eta_1(T_{w2})$ should be at least $10^3$ Poise, e.g., $10^4$ Poise or $10^5$ Poise, and no more than $10^7$ Poise. Moreover, as the drawn fiber cools the behavior of both materials should change from viscous to elastic at similar temperatures. In other words, the softening temperature of the two materials should be similar. For example, at the softening temperature of the second material, $T_{s2}$, the viscosity of the first material, $\eta_1(T_{s2})$ should be at least $10^6$ Poise, e.g., $10^7$ Poise or $10^8$ Poise and no more than $10^9$ Poise. In preferred embodiments, it should be possible to anneal both materials together, so at the annealing temperature of the second material, $T_{a2}$, the viscosity of the first material, $\eta_1(T_{a2})$ should be at least $10^8$ Poise (e.g., at least $10^9$ Poise, at least $10^{10}$ Poise, at least $10^{11}$ Poise, at least $10^{12}$ Poise, at least $10^{13}$ Poise, at least $10^{14}$ Poise).

Additionally, to be rheologically compatible, the change in viscosity as a function of temperature (i.e., the viscosity slope) for both materials should preferably match as close as possible.

A second selection criterion is that the thermal expansion coefficients (TEC) of each material should be similar at temperatures between the annealing temperatures and room temperature. In other words, as the fiber cools and its rheology changes from liquid-like to solid-like, both materials' volume should change by similar amounts. If the two materials TEC's are not sufficiently matched, a large differential volume change between two fiber portions can result in a large amount of residual stress buildup, which can cause one or more portions to crack and/or delaminate. Residual stress may also cause delayed fracture even at stresses well below the material's fracture stress.

The TEC is a measure of the fractional change in sample length with a change in temperature. This parameter can be calculated for a given material from the slope of a temperature-length (or equivalently, temperature-volume) curve. The temperature-length curve of a material can be measured using e.g., a dilatometer, such as a Model 1200D dilatometer from Orton Ceramic Foundation (Westerville, Ohio). The TEC can be measured either over a chosen temperature range or as the instantaneous change at a given temperature. This quantity has the units ° C.$^{-1}$.

For many materials, there are two linear regions in the temperature-length curve that have different slopes. There is a transition region where the curve changes from the first to the second linear region. This region is associated with a glass transition, where the behavior of a glass sample transitions from that normally associated with a solid material to that normally associated with a viscous fluid. This is a continuous transition and is characterized by a gradual change in the slope of the temperature-volume curve as opposed to a discontinuous change in slope. A glass transition temperature, $T_g$, can be defined as the temperature at which the extrapolated glass solid and viscous fluid lines intersect. The glass transition temperature is a temperature associated with a change in the materials rheology from a brittle solid to a solid that can flow. Physically, the glass transition temperature is related to the thermal energy required to excite various molecular translational and rotational modes in the material. The glass transition temperature is often taken as the approximate annealing point, where the viscosity is $10^{13}$ Poise, but in fact, the measured $T_g$ is a relative value and is dependent upon the measurement technique.

A dilatometer can also be used to measure a dilatometric softening point, $T_{ds}$. A dilatometer works by exerting a small compressive load on a sample and heating the sample. When the sample temperature becomes sufficiently high, the material starts to soften and the compressive load causes a deflection in the sample, when is observed as a decrease in volume or length. This relative value is called the dilatometric softening point and usually occurs when the materials viscosity is between $10^{10}$ and $10^{12.5}$ Poise. The exact $T_{ds}$ value for a material is usually dependent upon the instrument and measurement parameters. When similar instruments and measurement parameters are used, this temperature provides a useful measure of different materials rheological compatibility in this viscosity regime.

As mentioned above, matching the TEC is an important consideration for obtaining fiber that is free from excessive residual stress, which can develop in the fiber during the draw process. Typically, when the TEC's of the two materials are not sufficiently matched, residual stress arises as elastic Kress. The elastic stress component stems from the difference in volume contraction between different materials in the fiber as it cools from the glass transition temperature to room temperature (e.g., 25° C.). The volume change is determined by the TEC and the change in temperature. For embodiments in which the materials in the fiber become fused or bonded at any interface during the draw process, a difference in their respective TEC's will result in stress at the interface. One material will be in tension (positive stress) and the other in compression (negative stress), so that the total stress is zero. Moderate compressive stresses themselves are not usually a major concern for glass fibers, but tensile stresses are undesirable and may lead to failure over time. Hence, it is desirable to minimize the difference in TEC's of component materials to minimize elastic stress generation in a fiber during drawing. For example, in a composite fiber formed from two different materials, the absolute difference between the TEC's of each glass between $T_g$ and room temperature measured with a dilatometer with a heating rate of 3° C./min, should be no more than about $5 \times 10^{-6\circ}$ C.$^{-1}$ (e.g., no more than about $4 \times 10^{-6\circ}$ C.$^{-1}$, no more than about $3 \times 10^{-6\circ}$ C.$^{-1}$, no more than about $2 \times 10^{-6\circ}$ C.$^{-1}$, no more than about $1 \times 10^{-6\circ}$ C.$^{-1}$, no more than about $5 \times 10^{-7\circ}$ C.$^{-1}$, no more than about $4 \times 10^{-7\circ}$ C.$^{-1}$, no more than about $3 \times 10^{-7\circ}$ C.$^{-1}$, no more than about $2 \times 10^{-7\circ}$ C.$^{-1}$).

While selecting materials having similar TEC's can minimize an elastic stress component, residual stress can also develop from viscoelastic stress components. A viscoelastic stress component arises when there is sufficient difference between strain point or glass transition temperatures of the component materials. As a material cools below $T_g$ it undergoes a sizeable volume contraction. As the viscosity changes in this transition upon cooling, the time needed to relax stress increases from zero (instantaneous) to minutes. For example, consider a composite preform made of a glass and a polymer having different glass transition ranges (and different $T_g$'s). During initial drawing, the glass and polymer behave as viscous fluids and stresses due to drawing strain are relaxed instantly. After leaving the hottest part of the draw furnace, the fiber rapidly loses heat, causing the viscosities of the fiber materials to increase exponentially, along with the stress relaxation time. Upon cooling to its $T_g$, the glass and polymer cannot practically release any more stress since the stress relaxation time has become very large compared with the draw rate. So, assuming the component materials possess different $T_g$ values, the first material to cool to its $T_g$ can no longer reduce stress, while the second material is still above its $T_g$ and can release stress developed between the materials. Once the second material cools to its $T_g$, stresses that arise between the materials can no longer be effectively relaxed. Moreover, at this point the volume contraction of the second glass is much greater than the volume contraction of the first material (which is now below its $T_g$ and behaving as a brittle solid). Such a situation can result sufficient stress buildup between the glass and polymer so that one or both of the portions mechanically fail. This leads us to a third selection criterion for choosing fiber materials: it is desirable to minimize the difference in $T_g$'s of component materials to minimize viscoelastic stress generation in a fiber during drawing. Preferably, the glass transition temperature of a first material, $T_{g1}$, should be within 100° C. of the glass transition temperature of a second material, $T_{g2}$ (e.g., $|T_{g1}-T_{g2}|$ should be less than 90° C., less than 80° C., less than 70° C., less than 60° C., less than 50° C., less than 40° C., less than 30° C., less than 20° C., less than 10° C.).

Since there are two mechanisms (i.e., elastic and viscoelastic) to develop permanent stress in drawn fibers due to differences between constituent materials, these mechanisms may be employed to offset one another. For example, materials constituting a fiber may naturally offset the stress caused by thermal expansion mismatch if mismatch in the materials $T_g$'s results in stress of the opposite sign. Conversely, a greater difference in $T_g$ between materials is acceptable if the materials' thermal expansion will reduce the overall permanent stress. One way to assess the combined effect of thermal expansion and glass transition temperature difference is to compare each component materials' temperature-length curve. After finding $T_g$ for each material using the foregoing slope-tangent method, one of the curves is displaced along the ordinate axis such that the curves coincide at the lower $T_g$ temperature value. The difference in y-axis intercepts at room temperature yields the strain, $\in$, expected if the glasses were not conjoined. The expected tensile stress, $\sigma$ for the material showing the greater amount of contraction over the temperature range from $T_g$ to room temperature, can be computed simply from the following equation:

$$\sigma = E \cdot \in, \qquad (4)$$

where E is the elastic modulus for that material. Typically, residual stress values less than about 100 MPa (e.g., about 50 MPa or less, about 30 MPa or less), are sufficiently small to indicate that two materials are compatible.

A fourth selection criterion is to match the thermal stability of candidate materials. A measure of the thermal stability is given by the temperature interval $(T_x - T_g)$, where $T_x$ is the temperature at the onset of the crystallization as a material cools slowly enough that each molecule can find its lowest energy state. Accordingly, a crystalline phase is a more energetically favorable state for a material than a glassy phase. However, a material's glassy phase typically has performance and/or manufacturing advantages over the crystalline phase when it comes to fiber waveguide applications. The closer the crystallization temperature is to the glass transition temperature, the more likely the material is to crystallize during drawing, which can be detrimental to the fiber (e.g., by introducing optical inhomogeneities into the fiber, which can increase transmission losses). Usually a thermal stability interval, $(T_x-T_g)$ of at least about 80° C. (e.g., at least about 100° C.) is sufficient to permit fiberization of a material by drawing fiber from a preform. In preferred embodiments, the thermal stability interval is at least about 120° C., such as about 150° C. or more, such as about 200° C. or more. $T_x$ can be measured using a thermal analysis instrument, such as a differential thermal analyzer (DTA) or a differential scanning calorimeter (DSC).

A further consideration when selecting materials that can be co-drawn are the materials' melting temperatures, $T_m$. At the melting temperature, the viscosity of the material becomes too low to successfully maintain precise geometries during the fiber draw process. Accordingly, in preferred embodiments the melting temperature of one material is higher than the working temperature of a second, rheologically compatible material. In other words, when heating a preform, the preform reaches a temperature at it can be successfully drawn before either material in the preform melts.

One example of a pair of materials which can be co-drawn and which provide a photonic crystal fiber waveguide with high index contrast between layers of the confinement region are $As_2Se_3$ and the polymer PES. $As_2Se_3$ has a glass transition temperature $(T_g)$ of about 180° C. and a thermal expansion coefficient (TEC) of about $24 \times 10^{-6}/°$ C. At 10.6 µm, $As_2Se_3$ has a refractive index of 2.7775, as measured by Hartouni and coworkers and described in *Proc. SPIE*, 505, 11 (1984), and an absorption coefficient, $\alpha$, of 5.8 dB/m, as measured by Voigt and Linke and described in "Physics and Applications of Non-Crystalline Semiconductors in Optoelectronics," Ed. A. Andriesh and M. Bertolotti, NATO ASI Series, 3. High Technology, Vol. 36, p. 155 (1996). Both of these references are hereby incorporated by reference in their entirety. PES has a TEC of about $55 \times 10^{-6}/°$ C. and has a refractive index of about 1.65.

Embodiments of photonic crystal fibers and methods for forming photonic crystal fibers are described in the following patents and patent applications: U.S. Pat. No. 6,625,364, entitled "LOW-LOSS PHOTONIC CRYSTAL WAVEGUIDE HAVING LARGE CORE RADIUS;" U.S. Pat. No. 6,563,981, entitled "ELECTROMAGNETIC MODE CONVERSION IN PHOTONIC CRYSTAL MULTIMODE WAVEGUIDES;" U.S. patent application Ser. No. 10/057,440, entitled "PHOTONIC CRYSTAL OPTICAL WAVEGUIDES HAVING TAILORED DISPERSION PROFILES," and filed on Jan. 25, 2002; U.S. patent application Ser. No. 10/121,452, entitled "HIGH INDEX-CONTRAST FIBER WAVEGUIDES AND APPLICATIONS," and filed on Apr. 12, 2002; U.S. Pat. No. 6,463,200, entitled "OMNIDIRECTIONAL MULTILAYER DEVICE FOR ENHANCED OPTICAL WAVEGUIDING;" Provisional 60/428,382, entitled "HIGH POWER WAVEGUIDE," and filed on Nov. 22, 2002; U.S. patent application Ser. No. 10/196,403, entitled "METHOD OF FORMING REFLECTING DIELECTRIC MIRRORS," and filed on Jul. 16, 2002; U.S. patent application Ser. No. 10/720,606, entitled "DIELECTRIC WAVEGUIDE AND METHOD OF MAKING THE SAME," and filed on Nov. 24, 2003; U.S. patent application Ser. No. 10/733,873, entitled "FIBER WAVEGUIDES AND METHODS OF MAKING SAME," and filed on Dec. 10, 2003. The contents of each of the above mentioned patents and patent applications are hereby incorporated by reference in their entirety.

Figure 3:
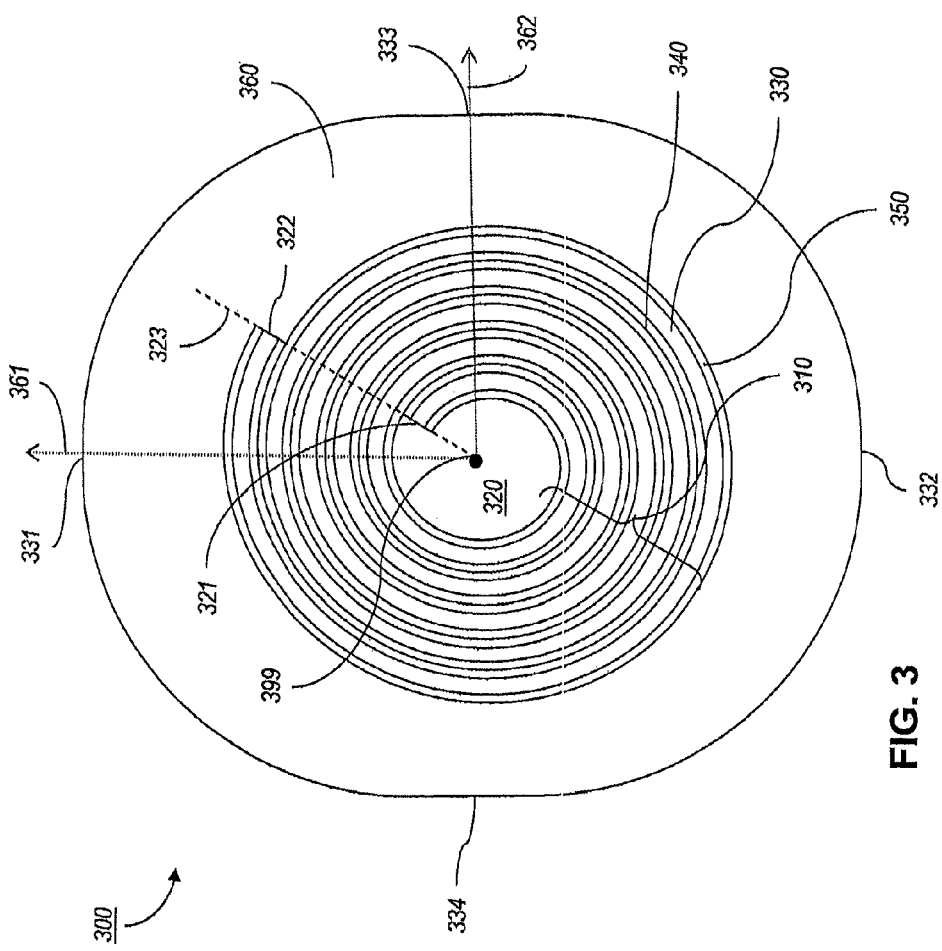
FIG. 3 is a cross-sectional view of a photonic crystal fiber including a cladding having an asymmetric cross-section.

Referring again to FIG. 1, in some embodiments, photonic crystal fiber 120 can be can be designed so that the fiber bends preferably in a certain plane. For example, referring to FIG. 3, a photonic crystal fiber 300 includes a cladding 360 that has an asymmetric cross-section with a larger diameter along a major axis 361 compared to its diameter along a minor axis 362 orthogonal to the major axis. The major and minor axes are orthogonal to axis 399. The asymmetric cross-section is also manifested in the shape of the cladding's outer surface, which includes portions of differing curvature. In particular, cladding 360 includes arcuate portions 331 and 332 and two straight portions 333 and 334. Arcuate portions 331 and 332 are on opposite sides of the cladding along major axis 321. Straight portions 333 and 334 are on opposite sides of the cladding along minor axis 322.

In general, the asymmetry of the cross-sectional profile of cladding 360 is sufficient to cause fiber 300 to preferably bend in a plane defined by fiber axis 399 and the minor axis 362 during normal use of the fiber.

The ratio of fiber 300's diameter along the major axis to its diameter along the minor axis can vary. Typically, this ration is selected so that fiber 300 bends preferably in the bend plane, while cladding 300 still provides the desired mechanical support or other function(s) for which it is designed (e.g., optical function, thermal management). In some embodiments, this ratio can be relatively low, such as about 1.5:1 or less (e.g., about 1.3:1 or less, about 1.1:1 or less). Alternatively, in certain embodiments, this ratio can be larger than about 1.5:1 (e.g., about 1.8:1 or more, about 2:1 or more).

Photonic crystal fiber 300 also includes a core 320 and a confinement region 310 that includes spiral layers 330, 340, and 350, and has an inner seam 321 and an outer seam 322 corresponding to the edges of the continuous layers from which the confinement region is formed. Inner seam 321 is located along an azimuth 323 that is displaced by an angle $\alpha$ from minor axis 362. $\alpha$ can be about 10° or more (e.g., about 20° or more, about 30° or more, about 40° or more, about 50° or more, about 60° or more, about 70° or more, about 80° or more). In some embodiments, $\alpha$ is about 90°.

The inner seam does not lie in the preferred bending plane of the fiber. In fiber 300, this is achieved by locating inner seam 321 away from the minor axis. Locating the inner seam away from the preferred bending plane car, be advantageous since it is believed that losses (e.g., due to scattering and/or absorption) of guided radiation is higher at the seam compared to other portions of the confinement region. Further, it is believed that the energy density of guided radiation in the core is higher towards the outside of a bend in the fiber relative to the energy density at other parts of the core. By locating the inner seam relative to the minor axis so that the seam is unlikely to lie in the preferred bending plane (e.g., where $\alpha$ is about 90°), the probability that the inner seam will lie towards the outside of a fiber bend is reduced. Accordingly, the compounding effect of having a relatively high loss portion of the confinement region at the region where the energy density of guided radiation is high can be avoided, reducing the loss associated with bends in the fiber.

Although inner seam 321 and outer seam 322 are positioned at the same azimuthal position with respect to axis 399 in fiber 300, in other embodiments the inner and outer seams can be located along at different relative azimuthal positions with respect to the fiber's axis.

As discussed previously, the cladding provides mechanical support for the fiber's confinement region. Accordingly, the thickness of cladding 360 can vary as desired along major axis 361. The thickness of cladding 360 along minor axis 362 can also vary but is generally less than the thickness along the major axis. In some embodiments, cladding 360 is substantially thicker along the major axis than confinement region 310. For example, cladding 360 can be about 10 or more times thicker than confinement region 310 (e.g., more than about 20, more than about 30, more than about 50 times thicker) along the major axis.

Fiber asymmetry can be introduced by shaving the perform, and then drawing the fiber from the perform that has an asymmetric cross-section. Alternatively, in some embodiments, the fiber asymmetry can be introduced after the fiber is drawn from a perform. For example, a fiber can be shaved or ground as part of the production process after being drawn but before being spooled.

Although fiber 300 includes a confinement region that has a seam, in general, embodiments of asymmetric fibers can include confinement regions with no seams (e.g., confinement regions that are formed from a number of annular layers).

Furthermore, while fiber 300 has a shape composed of two circular arcs and two straight lines, in general, fibers can have other shapes. For example, fibers can have asymmetric polygonal shapes, can be formed from arcuate portions having different radii of curvature, and/or from arcuate portions that curve in opposite directions. Generally, the shape should provide the fiber with a preferred bending plane.

While the foregoing fibers are asymmetric with respect to their cross-sectional shape, in general, fibers can be asymmetric in a variety of ways in order to provide a preferred bend plane. For example, in some embodiments, fibers can include material asymmetries that give rise to a preferred bend plane. Material asymmetries refer to variations between the material properties of different portions of a fiber that cause the fiber to bend preferably in a particular way. For example, a portion of a fiber cladding can be formed from a material that is mechanically less rigid that other portions, causing the fiber to bend preferably at that portion. Mechanical variations can be caused by compositional changes or by physical differences in portions having the same composition. Compositional differences can be introduced, e.g., by doping portions of a fiber or fiber preform with a dopant that alters the mechanical properties of a fiber. As another example, compositional differences can be introduced by forming different portions of a fiber from different compounds. Physical differences refer to, e.g., differences in the degree of crystallinity in different portions of a fiber. Physical differences, such as differences in crystallinity, can be introduced by selectively heating and/or cooling portions of a fiber during fiber fabrication, and/or using different rates of heating/cooling on different fiber portions.

Furthermore, in some embodiments, fibers can include a symmetric first cladding, but can include additional structure outside of the cladding that cause the fiber to bend preferably in a particular plane. For example, fibers can be placed in one or more sheaths that are asymmetric when it comes to allowing the fiber to bend.

Referring again to FIG. 1, laser system 100 also includes a cooling apparatus 170, which delivers a cooling fluid (e.g., a gas or a liquid) to fiber 120 via a delivery tube 171 and coupling assembly 130. The cooling fluid is pumped through the core and absorbs heat from the fiber surface adjacent the core. In the present embodiment, the cooling fluid flows in the same direction as the radiation from laser 110, however, in some embodiments, the cooling fluid can be pumped counter to the direction of propagation of the laser radiation.

The flow rate of the cooling fluid through the core of photonic crystal fiber 120 can vary as desired. Typically, the flow rate depends on the operating power of the laser, the absorption of the fiber at the operating wavelength, the length of the fiber, and the size of the fiber core, for example. Generally, the flow rate should be sufficient to cool the fiber at its operating power. In some embodiments, the flow rate can be about 0.1 liters/min or more (e.g., about 0.5 liters/min or more, about 1 liter/min or more, about 2 liters/min or more, about 5 liters/min or more, about 8 liters/min or more, about 9 liters/min or more, about 10 liters/min or more).

The pressure of cooling fluid exhausted from the fiber can vary. In some embodiments, the pressure of the cooling fluid can be relatively high. For example, where the fluid exits from the same end of the fiber as the radiation, a cooling gas can be at sufficiently high pressure to clear debris from the target tissue of the patient. The gas pressure can be about 0.2 PSI or more (e.g., about 0.5 PSI or more, about 1 PSI or more). In some embodiments, the pressure of a gas exiting the core of a fiber can correspond to a flow rate of about 1 liter/min or more (e.g., about 2 liter/min or more, about 5 liter/min or more, about 8 liter/min or more, about 10 liter/min or more) through a 1 meter length of fiber having a core diameter of about 500 μm.

The flow rate can be nominally constant while the system is activated, or can vary depending on the state operation of the laser system. For example, in some embodiments, the flow rate can be adjusted based on whether radiation is being directed through fiber 120 or not. At times where the laser is activated and radiation is directed through the fiber, the flow rate can be at a level sufficient to adequately cool the fiber. However, between radiation doses, the system can reduce the flow rate to a lower level (e.g., about 10% or less than the rate used to cool the fiber while the laser is activated). The gas flow rate can be triggered using remote control 152 or an additional remote control that the operator can easily operate while using the system.

In general, the temperature of the cooling fluid directed to the fiber can vary. In some embodiments, the cooling fluid is directed to the fiber at ambient temperature (e.g., at room temperature). In certain embodiments, the cooling fluid is cooled below ambient temperature prior to cooling the fiber. The cooling fluid can be cooled so that fluid exhausted from the fiber is within a certain temperature range. For example, the cooling fluid can be sufficiently cooled so that fluid exhausted from the fiber does not scald the patient if it comes into contact with the patient. As another example, the cooling fluid can be sufficiently cooled so that fluid exhausted from the fiber is between room temperature and body temperature. In some embodiments, the cooling fluid directed to the fiber can be cooled so that it has a temperature below room temperature. For example, the fluid can have a temperature of about 20° C. or less (e.g., about 10° C. or less, about 0° C. or less, about −10° C. or less, about −20° C. or less, about −50° C. or less).

In certain embodiments, where the cooling fluid flows through the fiber core in the laser radiation propagation direction, it can perform additional functions where it impinges on the target tissue of the patient. For example, in some embodiments, heated fluid (e.g., gas) exiting the fiber can reduce bleeding it incised blood vessels (or other tissue) by enhancing coagulation of the blood. It is believed that coagulation of blood is accelerated at temperatures of about 60° C. or more. Accordingly, where the gas exiting the fiber impinging the target tissue is about 60° C. or more, it can increase the rate at which blood coagulates, which can assist the surgeon by reducing the need to suction blood from the operating area. In some embodiments, the temperature of gas exiting the fiber can be, for example, about 50° C. or more, about 60° C. or more, about 65° C. or more, about 70° C. or more, about 80° C. or more, about 90° C. or more, about 100° C. or more). Alternatively, in certain embodiments, the temperature of the gas exiting the fiber can be below room temperature (e.g., about 10° C. or less, about 0° C. or less). For example, the system can provide cooled gas to the target location in procedures where it is beneficial to cool tissue before irradiating the tissue. In certain embodiments, the temperature of gas exiting the fiber can be approximately at body temperature (e.g., at about 37° C.), Gas flowing through the fiber core can be healed by about 5-10° C./Watt of input power (e.g., about 7-8° C./Watt). For example, a fiber having an input power of about 20 Watts could heat gas flowing through its core by about 100-200° C.

In some embodiments, the fluid flowing through the fiber's core can be used to deliver other substances to the target tissue. For example, atomized pharmaceutical compounds could be introduced into a gas that is flowed through the core and delivered via the photonic crystal fiber to the target tissue.

In general, the type of cooling fluid can vary as desired. The cooling fluid can be liquid, gas, or superfluid. In some embodiments, the cooling fluid includes a noble gas (e.g., helium, neon, argon, krypton, and/or xenon), oxygen, carbon dioxide, and/or nitrogen. The cooling fluid can be composed substantially of a single compound (e.g., having a purity of about 98% or more, about 99% or more, about 99.5% or more, about 99.8% or more, about 99.9% or more), or can be a mixture (e.g., air or heliox).

In some embodiments, the cooling fluid is selected based on its ability to cool the fiber. The cooling ability of a fluid can depend on the fluids flow rate and/or the fluids thermal conductivity. Helium gas, for example, has a relatively high thermal conductivity compared to other gases. Furthermore, for a given pressure drop, helium can have a higher flow rate than other gases, such as nitrogen. Accordingly, in some embodiments, helium can be selected based on its ability to cool the fiber better than other gases.

Alternatively, or additionally, the cooling fluid can be selected based on whether or not it has any adverse interactions with the patient. For example, in embodiments where the cooling fluid is in close proximity to the patient, it can be selected based on its relatively low toxicity. In certain embodiments, a cooling fluid can be selected based on its solubility compared to other fluids. A fluid with relatively low solubility in blood can reduce the risk of the patient having an embolism due to exposure to the cooling fluid. An example of a fluid with relatively low toxicity and relatively low solubility is helium gas.

The cooling fluid can also be selected based on other criteria, such as its reactivity with other elements (e.g., flammability). In some embodiments, a cooling fluid, such as helium, can be selected based on its inert characteristics (e.g., inflammability).

In certain embodiments, a protective sleeve can be attached to the output end of photonic crystal fiber 120. Sleeves can be used to prevent debris buildup and clogging of the fiber's output end. An example of a sleeve 401 is shown in FIG. 4A. Sleeve 401 is attached to the output end of a photonic crystal fiber 410. Sleeve 401 includes a collar 425 that maintains a stand off distance 405 between the output end of the fiber and a distal opening 430 of the sleeve. Typically, stand off distance 405 is from about 0.5 cm to about 4 cm long. Radiation 411 exiting core 420 of fiber 410 exits the sleeve through distal opening 430.

Sleeve 401 can also include perforations to reduce the pressure of fluid exiting the fiber at distal opening 430. For example, sleeve 401 includes secondary openings 435 and 436 that, along with distal opening 430, provide paths through which fluid exiting core 420 can exit the sleeve.

Typically, sleeves are formed from rigid materials that can be readily sterilized. For example, sleeves can be formed from stainless steel. Sleeves can be disposable or reusable.

Another example of a sleeve is sleeve 401A shown in FIG. 4B. Sleeve 401A narrows along its length, having a larger diameter 402B where it attaches to the output end of fiber 401 compared to the diameter 402A near the distal opening. The narrowing sleeve increases the pressure of fluid from core 420 in the sleeve, increasing the fluid pressure at openings 435A and 435B, thereby reducing the possibility of debris being sucked into the sleeve through these openings.

In some embodiments, sleeves can include one or more optical components. For example, referring to FIG. 4C, a sleeve 401B can include a reflector 440 (e.g., a mirror) attached near the distal opening. Reflector 440 redirects radiation 411 exiting core 420, and can enable an operator to direct the radiation into confined spaces not otherwise accessible.

In embodiments, sleeves can also include transmissive optical components. For example, referring to FIG. 4D, a sleeve 401C includes a lens 450 mounted near distal opening 430. Lens is mounted within the sleeve by a lens mount 451, which is positioned between distal opening 430 and secondary openings 435 and 436 so that fluid from the fiber can still exit sleeve 401C through openings 435 and 436. Lens 450 focuses radiation 411 exiting core 420 to a waist at some position beyond distal opening 430. Another example of a transmissive optical component that can be mounted within a sleeve is a transmissive optical flats, which can serve as a window for the transmission of radiation exiting the fiber core while preventing fluid flow through distal opening 430.

Figures 5A, 5B:
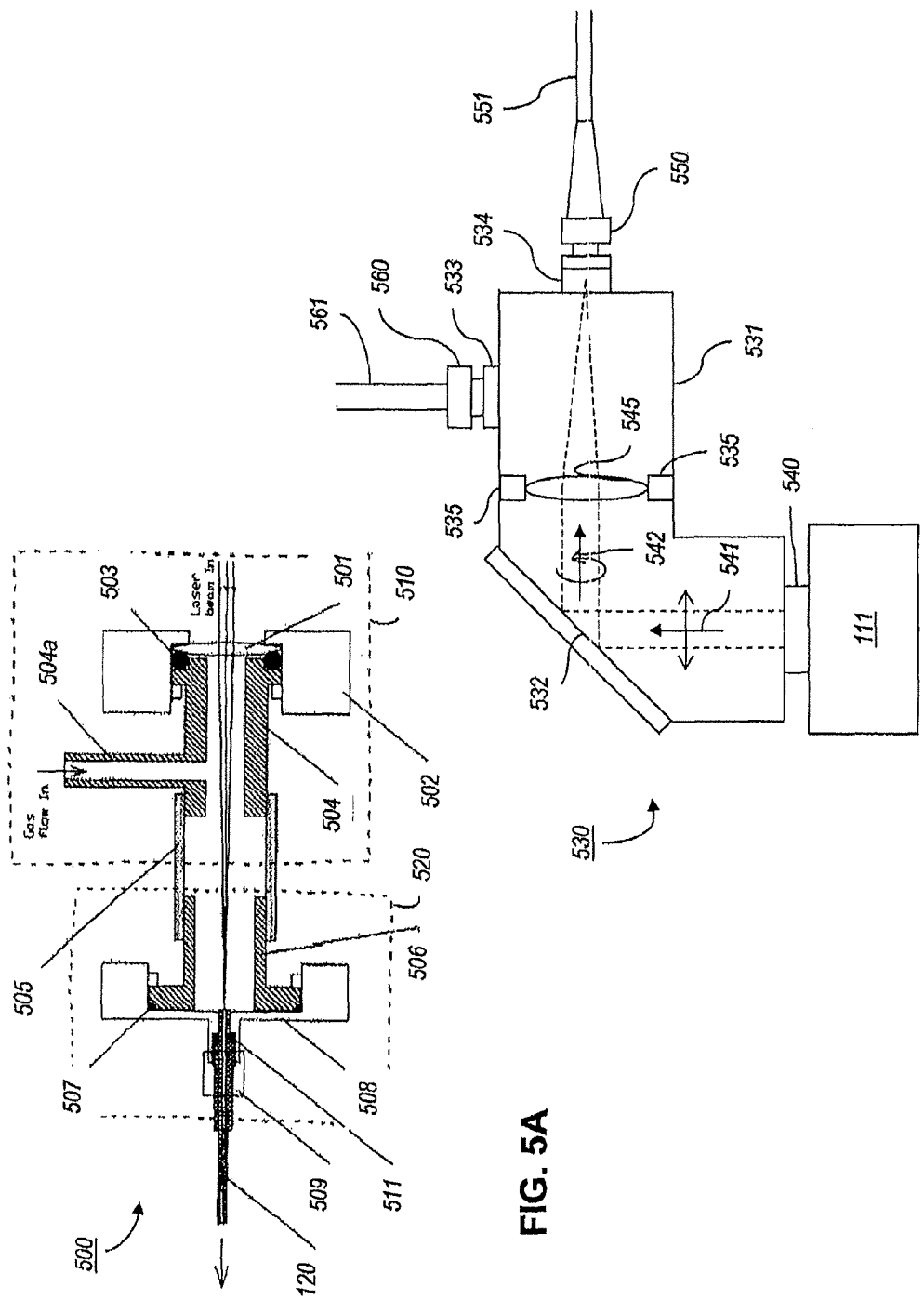
FIGS. 5A and 5B are diagrams of embodiments of coupling assemblies for coupling radiation and a fluid into a hollow core of a photonic crystal fiber.

As discussed previously, in laser system 100, light is coupled from laser 110 and fluid from fluid source 170 into fiber 120 by coupling assembly 130. Referring to FIG. 5A, an example of a coupler for coupling gas and radiation into a photonic crystal fiber is coupling assembly 500. Coupling assembly 500 includes a first portion 510 that receives radiation from the laser and gas from a gas source, and a second portion 520 that connects to photonic crystal fiber 120. First portion 510 is coupled to second portion 520 by a flexible junction 505 (e.g., a metallic bellows or rubber tube).

First portion 510 includes a lens holder 502 and an adaptor 504 for the lens holder. The lens holder can be a commercially available lens holder. When coupled to lens holder 5-2, adaptor 504 secures a lens 501 in the lens holder. An o-ring 503 creates a seal between adaptor 504 and lens 501. Adaptor 504 also includes a fitting 504a for connecting to tube that supplies gas to the system. In some embodiments, fitting 504a includes a barbed hose fitting.

Portion 520 includes a connector alignment stage 508 including a fiber optic connector receptacle (e.g., a commercially available Kage, such as component LP-1A, available from Newport (Irvine, Calif.)). Stage 508 is connected to flexible junction 505 by an adaptor 506. An o-ring 507 creates a seal between stage 508 and adaptor 506. A fiber optic connector 509 couples photonic crystal fiber 510 to stage 58. Another o-ring 511 creates a seal between fiber optic connector 509 and stage 508.

Another example of a coupling assembly is shown in FIG. 5B. Coupling assembly 530 includes a laser connector 540 that attaches to the output terminal 111 of laser 110. Coupling assembly 530 includes a housing 531 attached to laser connector 540. The housing includes a fluid inlet port 533 and a radiation output port 534. A fiber optic connector 550 affixes to radiation output port 534, positioning an end of a photonic crystal fiber 551 relative to the radiation output port. In addition, a connector 560 connects a fluid conduit 561 to the housing by attaching to fluid input port 533.

A retardation reflector 532 is positioned within housing 531. Retardation reflector 532 directs linearly polarized radiation 541 entering the housing from the laser towards a radiation output terminal 534, modifying the polarization state so that reflected radiation 542 is circularly polarized. More generally, the reflective retarder modifies the polarization state of the laser radiation to provide a lower loss polarization to fiber 551. In embodiments, average losses of circularly polarized radiation may be lower than linearly polarized radiation where the fiber has high loss regions that may be coincident with the plane of polarization. For example, photonic crystal fibers that have a confinement region having a seam can exhibit higher losses for radiation polarized in the plane of the seam compared to circularly polarized light. Alternatively, or additionally to having a retarder, fiber 551 can be attached with its seam (or other high loss region) in a particular orientation with respect to the polarization state of radiation from the laser.

Examples of a reflective retarder suitable for 10.6 micron radiation are series PRR: Silicon & Copper Phase Retardation Reflectors (commercially-available from Laser Research Optics (Providence, R.I.). Transmissive retarders (e.g., formed from birefringent crystals) can be used in place of, or in addition to, retardation reflector 532.

Coupling assembly 530 also includes a lens 545, mounted within housing 531 by mount 535, which focuses reflected radiation 542 to a waist at radiation output port 534 where it couples into the core of fiber 551. Lenses suitable for use at 10.6 micron wavelengths, for example, can be formed from ZnSe.

In embodiments where cooling fluid is not coupled into the fiber's core, other coupling assemblies can be used. Generally, in such embodiments, any coupler suitable for the wavelength and intensity at which the laser system operates can be used. One type of a coupler is described by R. Nubling and J. Harrington in "Hollow-waveguide delivery systems for high-power, industrial $CO_2$ lasers," Applied Optics, 34, No. 3, pp. 372-380 (1996). Other examples of couplers include one or more focusing elements, such as one or more lenses. More generally, the coupler can include additional optical components, such as beam shaping optics, beam filters and the like.

In general, coupling efficiency can be relatively high. For example, coupling assembly 130 can couple more than about 70% of the laser output at the guided wavelength into a guided mode in the fiber (e.g., about 80% or more, 90% or more, 95% or more, 98% or more). Coupling efficiency refers to the ratio of power guided away by the desired mode to the total power incident on the fiber.

While laser system 100 includes handpiece 140, systems can include different types of handpieces depending on the medical application for which they are being used. In general, a handpiece includes a portion that the operator can grip, e.g., in his/her palm or fingertips, and can include other components as well. In certain embodiments, handpieces can include endoscopes (e.g., flexible or rigid endoscopes), such as a cystoscopes (for investigating a patient's bladder), nephroscopes (for investigating a patient's kidney), bronchoscopes (for investigating a patient's bronchi), laryngoscopes (for investigating a patient's larynx), otoscopes (for investigating a patient's ear), arthroscopes (for investigating a patient's joint), laparoscopes (for investigating a patient's abdomen), and gastrointestinal endoscopes. Another example of a handpiece is a catheter, which allows an operator to position the output end of the photonic crystal fiber into canals, vessels, passageways, and/or body cavities.

Moreover, handpieces can be used in conjunction with other components, without the other component being integrated into the handpiece. For example, handpieces can be used in conjunction with a trocar to position the output end of a photonic crystal fiber within an abdominal cavity of a patient. In another example, a handpiece can be used in conjunction with a rigid endoscope, where the rigid endoscope is not attached to the gripping portion of the handpiece or to the photonic crystal fiber.

Figure 6:
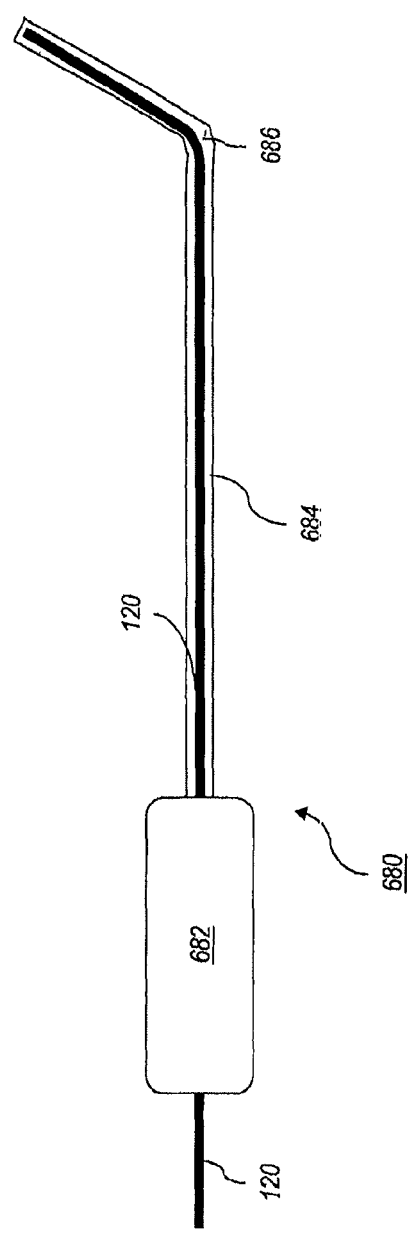
FIG. 6 is a diagram of a handpiece that includes a malleable conduit.

Referring to FIG. 6, in some embodiments, a handpiece 680 includes a narrow conduit 684 that includes a channel through which photonic crystal fiber 120 is inserted. Conduit 684 can be made from a rigid, but deformable, material (e.g., stainless steel). This allows the operator to bend the conduit (e.g., by hand or using a tool) to a desired amount (e.g., such as at bend 686) for a procedure, where the conduit retains the bend until the operator straightens it or bends it in a different way. Handpiece 680 also includes a gripping portion 682 attached to conduit 684, which allows the operator to comfortably hold the handpiece.

Figure 7A:
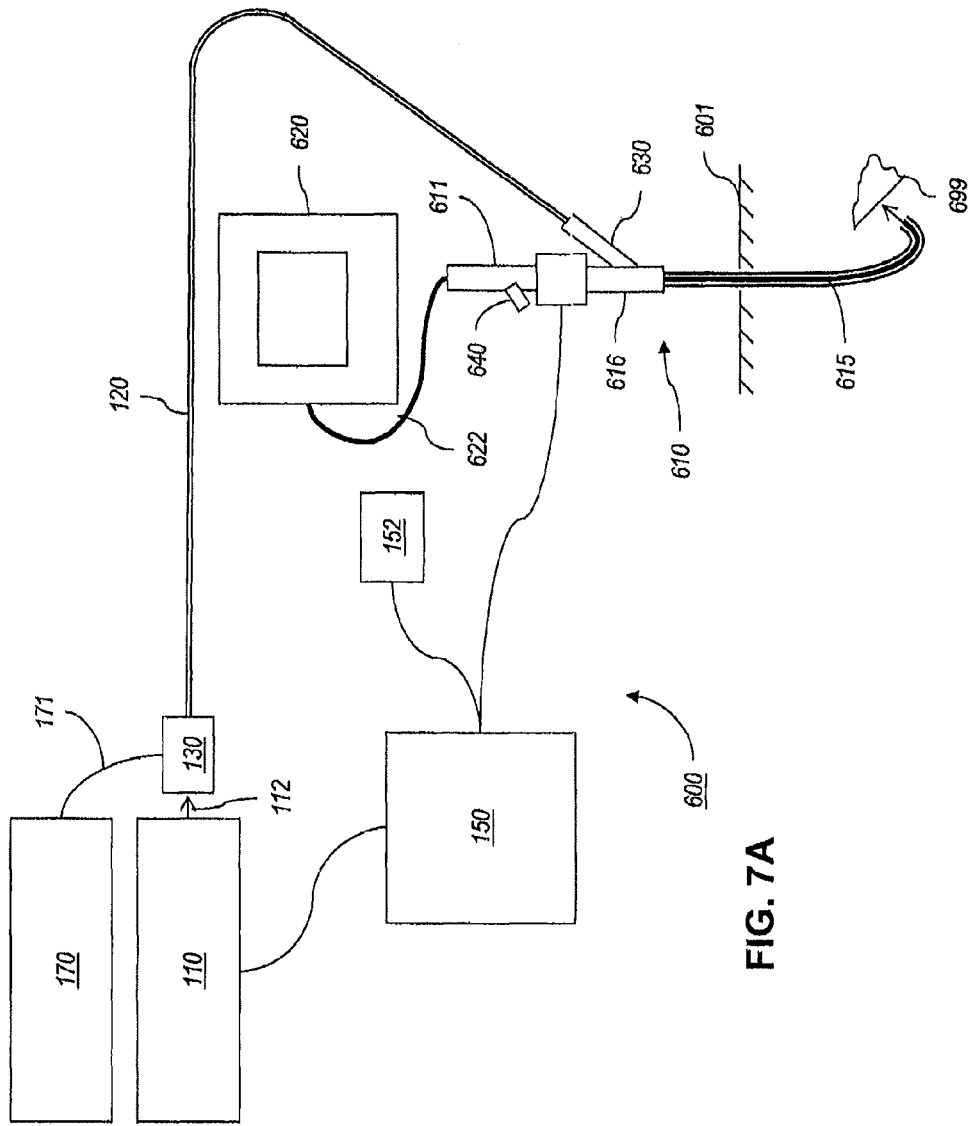
FIG. 7A is a schematic diagram of another embodiment of a laser medical system including a photonic crystal fiber.

In certain embodiments, handpieces can include actuators that allow the operator to bend the fiber remotely, e.g., during operation of the system. For example, referring to FIG. 7A, in some embodiments, laser radiation 112 can be delivered to target tissue 699 within a patient 601 using an endoscope 610. Endoscope 610 includes a gripping portion 611 and a flexible conduit 615 connected to each other by an endoscope body 616. An imaging cable 622 housing a bundle of optical fibers is threaded through a channel in gripping portion 611 and flexible conduit 615. Imaging cable 622 provide illumination to target tissue 699 via flexible conduit 615. The imaging cable also guides light reflected from the target tissue to a controller 620, where it is imaged and displayed providing visual information to the operator. Alternatively, or additionally, the endoscope can include an eyepiece lens that allows the operator to view the target area directly through the imaging cable.

Endoscope 610 also includes an actuator 640 that allows the operator to bend or straighten flexible conduit 615. In some embodiments, actuator 640 allows flexible conduit 615 to bend in one plane only. Alternatively, in certain embodiments, the actuator allow the flexible conduit to bend in more than one plane.

Endoscope 610 further includes an auxiliary conduit 630 (e.g., a detachable conduit) that includes a channel through which fiber 120 is threaded. The channel connects to a second channel in flexible conduit 615, allowing fiber 120 to be threaded through the auxiliary conduit into flexible conduit 615. Fiber 120 is attached to auxiliary conduit in a matter than maintains the orientation of the fiber with respect the channel through flexible conduit 615, thereby minimizing twisting of the photonic crystal fiber about its waveguide axis within the flexible conduit. In embodiments where photonic crystal fiber 120 has a confinement region that includes a seam, the fiber can be attached to the auxiliary conduit so that the seam is not coincident with a bend plane of the flexible conduit.

In general, photonic crystal fibers can be used in conjunction with commercially-available endoscopes, such as endoscopes available from PENTAX Medical Company (Montvale, N.J.) and Olympus Surgical & Industrial America, Inc. (Orangeburg, N.Y.).

Figure 7B:
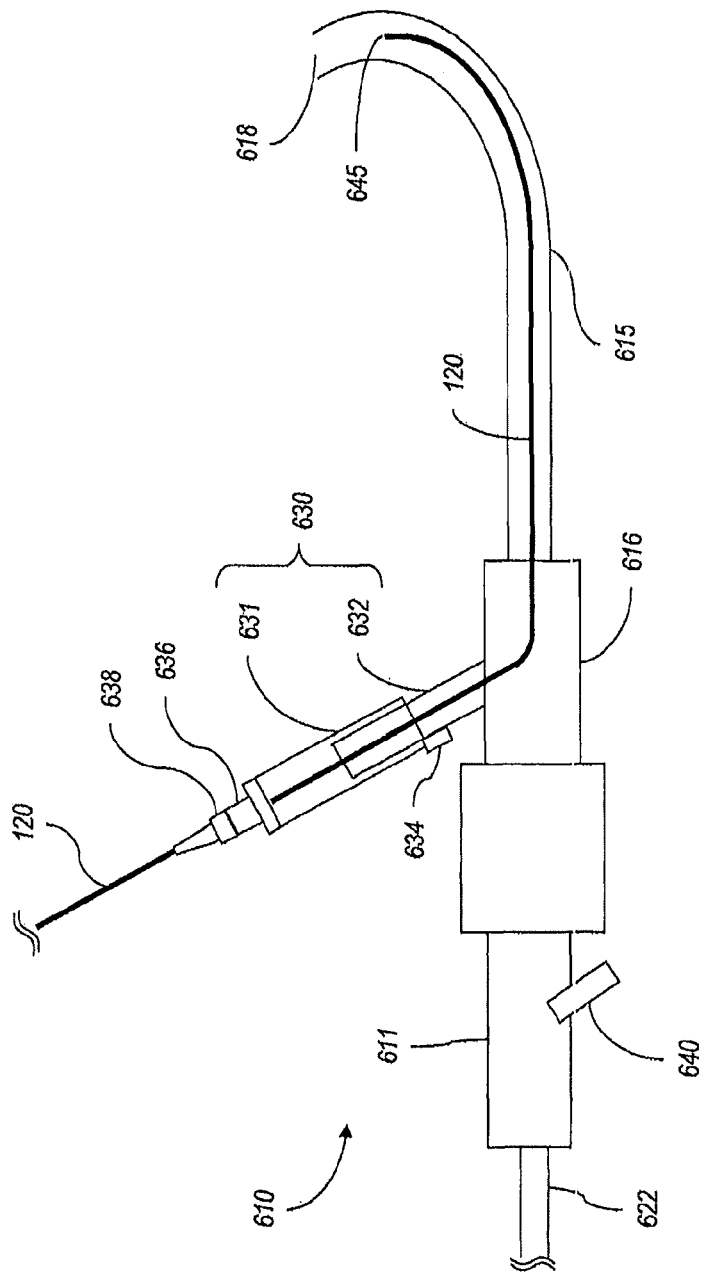
FIG. 7B is a diagram of an endoscope.

Auxiliary conduit 630 can be configured to allow the user to extend and/or retract the output end of the photonic crystal fiber within flexible conduit 615. For example, referring to FIG. 7B, in some embodiments, auxiliary conduit 630 of endoscope 610 can include two portions 631 and 632 that are moveable with respect to each other. Portion 632 is attached to endoscope body 616, while portion 631 telescopes with respect to portion 632. Portion 632 includes a connector 636 that connects to a fiber connector 638 attached to fiber 120. The mating mechanism of connector 636 and fiber connector 638 can allow for quick and simple removal and attachment of the photonic crystal fiber to the endoscope. When attached, connector 636 and fiber connector 638 substantially prevent fiber 120 from twisting, maintaining its orientation about the fiber axis within flexible conduit 615. The connectors can maintain the orientation of the fiber in the conduit with a seam in the fiber oriented away from a bend plane of the conduit, for example. Furthermore, when portion 631 extends or retracts with respect to portion 632, it extends or retracts the output end 645 of fiber 120 with respect to the distal end 618 of flexible conduit 615. Auxiliary conduit 630 also includes a locking mechanism 634 (e.g., a latch or clamp) that allows the user to lock the portion 631 with respect to portion 632. The locking mechanism prevents unwanted movement of fiber 120 within flexible conduit 615 while radiation is being delivered to the patient.

Figure 7C:
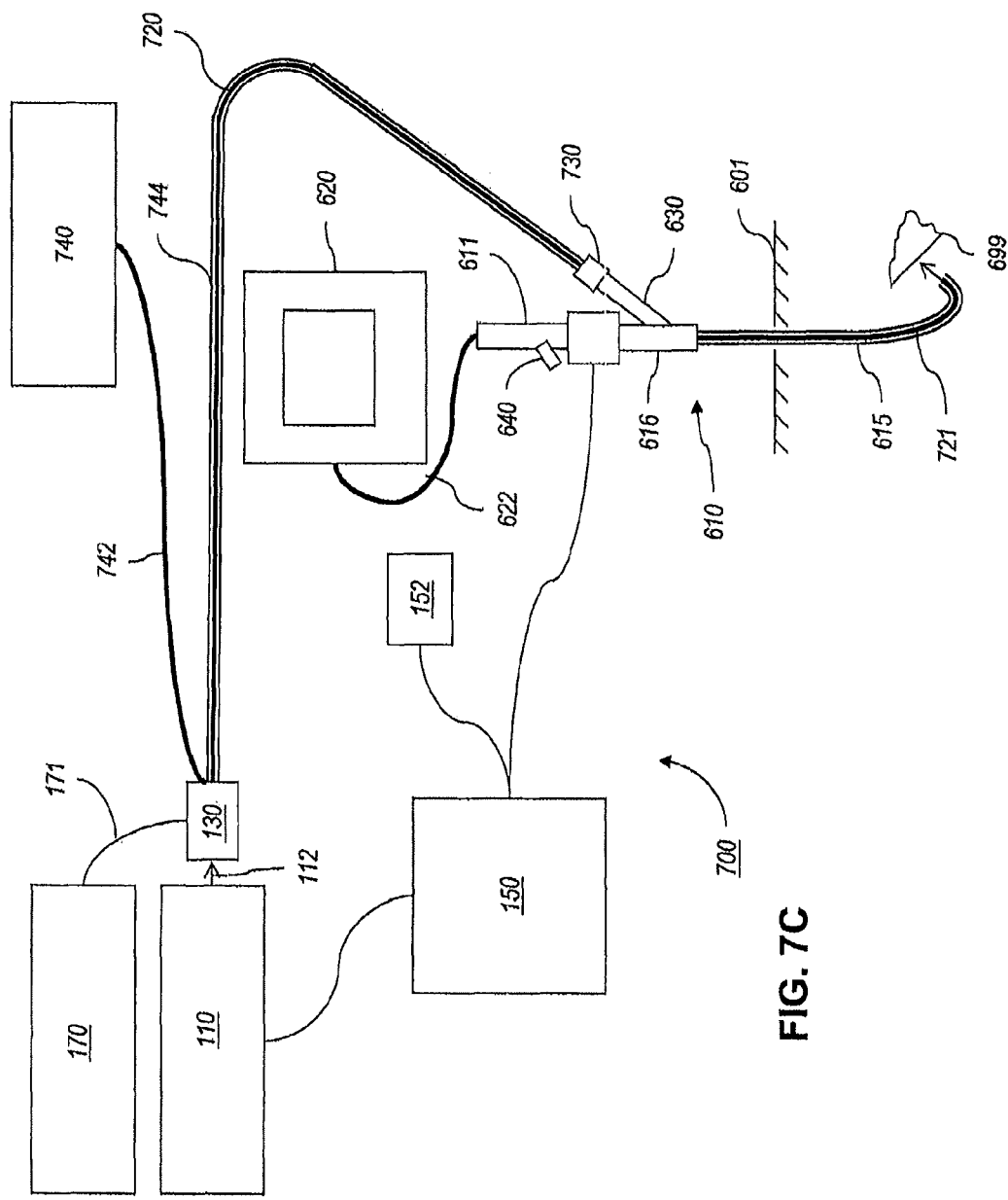
FIG. 7C is a schematic diagram of a further embodiment of a medical laser system including a photonic crystal fiber.

While laser systems 100 and 600 include a single length of a photonic crystal fiber that delivers radiation from laser 110 to the target location, multiple connected lengths of photonic crystal fiber can also be used. For example, referring to FIG. 7C, a laser system 700 includes two lengths of photonic crystal fiber 720 and 721 rather than a single length of photonic crystal fiber as laser systems 100 and 600. Photonic crystal fiber lengths 720 and 721 are coupled together by a connector 730 that attaches to auxiliary conduit 630 of endoscope 610.

Laser system 700 includes a secondary cooling apparatus 740 in addition, or alternatively, to cooling apparatus 170. Photonic crystal fiber length 720 is placed within a sheath 744, which is connected to secondary cooling apparatus 740 by a delivery tube 742. Secondary cooling apparatus 740 cools photonic crystal fiber length 720 by pumping a cooling fluid through sheath 744.

Secondary cooling apparatus 740 can recirculate the cooling fluid it pumps through sheath 744. For example, sheath 744 can include an additional conduit that returns the cooling fluid to secondary cooling apparatus 740. A heat exchanger provided with the secondary cooling system can actively cool the exhausted cooling fluid before the secondary cooling system pumps the fluid back to sheath 744.

The cooling fluid can be the same or different as the cooling fluid pumped into the core of the photonic crystal fiber by cooling apparatus 170. In some embodiments, cooling apparatus 170 pumps a gas through the core of the fiber, while secondary cooling apparatus 740 cools the fiber using a liquid (e.g., water).

Sheath 744 can perform a protective function, shielding photonic crystal fiber length 720 from environmental hazards. In some embodiments, sheath 744 includes a relatively rigid material (e.g., so that sheath 744 is more rigid than photonic crystal fiber length 720), reducing flexing of photonic crystal fiber length 720. In some embodiments, sheath 744 is formed from a relatively rigid material, such as nitinol (commercially-available from Memry, Inc., Bethel, Conn.).

In embodiments, using two lengths of photonic crystal fiber can prolong the usable lifetime of at least one of the lengths. For example, due to the additional cooling and/or protection afforded the fiber length by cooling apparatus 740 and/or sheath 744, photonic crystal fiber length 720 can be replaced less often than fiber length 721. In some embodiments, fiber length 721 can be used multiple times, while fiber length 721 is discarded after each use.

While laser system 700 utilizes two connected lengths of photonic crystal fiber, more generally, waveguides other than photonic crystal waveguides can also be connected to a length of photonic crystal fiber to provide a conduit for delivering radiation from a laser to the target location. For example, a length of a hollow metallic waveguide can be connected to a length of a photonic crystal fiber to provide a conduit for IR radiation.

Furthermore, in general, other conduits can be bundled with photonic crystal fibers in a medical laser system to, e.g., deliver something to, remove something from, or to observe the target tissue during the procedure. For example, as discussed in reference to FIG. 7A, the photonic crystal fiber can be bundled with other optical waveguides, such as an imaging cable used to illuminate and/or image the target tissue using an imaging system. In certain embodiments, laser systems can deliver radiation from more than one radiation source to the patient by delivering radiation. From a laser radiation through the photonic crystal fiber, and radiation from a second source (e.g., a second laser) through the other conduit (e.g., an optical fiber). As an example, referring to FIG. 8, in certain embodiments, a system 800 includes a fiber waveguide 830 and a photonic crystal fiber 810, with a portion of fiber waveguide 830 and photonic crystal fiber 810 being bundled within a jacket 850 (e.g., a flexible jacket, such as a flexible polymer jacket). Photonic crystal fiber 810 is coupled to a laser 820, which delivers radiation at wavelength $\lambda_1$ through the core 812 of photonic crystal fiber 810. Fiber waveguide 830 is coupled to another radiation source 840, which delivers radiation at a different wavelength, $\lambda_2$, through the core 832 of fiber waveguide 830. Photonic crystal fiber 810 and fiber waveguide 830 deliver radiation (indicated by reference numerals 822 and 842, respectively) at wavelengths $\lambda_1$ and $\lambda_2$, respectively, to a common location.

Fiber waveguide 830 can be, for example, an optical fiber or a photonic crystal fiber. Radiation source 840 can be a laser or other light source (e.g., a bulb or light emitting diode). As an example, in some embodiments, radiation source 840 is a laser that emits visible radiation (e.g., $\lambda_2$ is within a range from about 400 nm to about 800 nm, such as 633 nm), such as a HeNe laser and fiber waveguide 830 is an optical fiber. The visible radiation emitted from fiber 830 allows the operator to aim the output end of the photonic crystal fiber to the appropriate tissue before delivering laser radiation from laser 820. In another example, the other radiation source 840 is an Nd:YAG laser, which can also be used to deliver radiation to the patient for photocoagulation or photoablation purposes.

Jacket 850 can have a sufficiently small outer diameter to allow the jacket to be used in conjunction with a variety of handpieces. For example, the jacket can have an outer diameter of about 2 mm or less, allowing the jacket to be inserted into a standard-size channel of an endoscope.

In some embodiments, the photonic crystal fiber can be bundled with a tube for delivering gas to (e.g., hot gas for blood coagulation) or vacuuming debris at the target location, as an alternative or in addition to being bundled with a fiber waveguide.

For example, referring to FIG. 9, a system 900 a photonic crystal fiber 910 is bundled with a tube 930 for exhausting fluid (e.g., cooling fluid) exiting the photonic crystal fiber's core 912 at the fiber's output end. The system shown in FIG. 9 includes a laser 920 and a fluid source 926 that deliver radiation and fluid to the photonic crystal fiber's core 912 via a coupling assembly 924. The system also includes a pump that draws fluid exiting core 912 through tube 930 away from the patient.

The output end of fiber 910 and input end of tube 930 are coupled together by a cap 960, that fits over the ends of the fiber and tube. Cap 960 includes a window 962 that is made from a material substantially transparent to the wavelength of radiation being delivered from laser 920. Cap 960 positions window 962 in the path of radiation 922 exiting core 912, allowing the system to deliver the radiation to the patient. Fluid exiting core 912, however, is drawn through an exhaust port 964 into tube 942. Pump 940, connected to the opposite end of tube 930, draws the fluid 942 through the tube away from the patient.

A portion of tube 930 and photonic crystal fiber 910 are bundled together within a jacket 950, providing a flexible duct that can be threaded through a channel in a handpiece (e.g., a handpiece including an endoscope).

System 900 can be used in procedures where it is undesirable to exhaust fluid (e.g., cooling fluid) to the tissue being exposed to radiation. For example, where the radiation is being delivered internally, where the exhausted fluid is toxic, or is at an undesirable temperature (e.g., sufficiently hot to burn the exposed tissue), an exhaust tube can be included with the photonic crystal fiber to prevent exposure of the tissue to the fluid.

In some cases, the handpiece in a medical laser system can be replaced by a robot, which can be operated remotely. For example, robot-performed surgery is under consideration in applications where a surgeon cannot easily or rapidly reach a patient (e.g., a wounded soldier on a battlefield).

Since photonic crystal fibers are used in medical procedures, they should be sterilizable. For example, photonic crystal fibers should be able to withstand sterilizing procedures, such as autoclaving. Typically, lengths of photonic crystal fiber are provided to the user pre-sterilized and sealed in a container (e.g., vacuum sealed in a container that has sufficient barrier properties to prevent contamination of the fiber length during storage and shipping). For example, sterilized lengths of photonic crystal fiber (e.g., about 0.5 meters to about 2.5 meters lengths) can be provided sealed (e.g., vacuum sealed) in a plastic container (e.g., including a barrier film layer).

In general, the laser systems described above can be used in a number of different medical applications. Generally, the type of laser, wavelength, fiber length, fiber outer diameter, and fiber inner diameter, among other system parameters, will be selected according to the application. Medical applications include aesthetic medical procedures, surgical medical procedures, ophthalmic procedures, veterinary procedures, and dental procedures.

Aesthetic procedures include treatment for: hair removal; pulsed light skin treatments for reducing fine wrinkle lines, sun damage, age spots, freckles, some birthmarks, rosacea, irregular pigmentation, broken capillaries, benign brown pigment and pigmentation; skin resurfacing; leg veins; vascular lesions; pigmented lesions; acne; psoriasis & vitiligo; and/or cosmetic repigmentation.

Surgical procedures include procedures for gynecology, laparoscopy, condylomas and lesions of the external genitalia, and/or leukoplakia. Surgical applications can also include ear/nose/throat (ENT) procedures, such as laser assisted uvula palatoplasty (LAUP) (i.e., to stop snoring); procedures to remove nasal obstruction; stapedotomy; tracheobronchial endoscopy; tonsil ablation; and/or removal of benign laryngeal lesions. Surgical applications can also include breast biopsy, c ytoreduction for metastatic disease, treatment of decubitus or statis ulcers, hemorrhoidectomy, laparoscopic surgery, mastectomy, and/or reduction mammoplasty. Surgical procedures can also include procedures in the field of podiatry, such as treatment of neuromas, periungual, subungual and plantar warts, porokeratoma ablation, and/or radical nail excision. Other fields of surgery in which lasers may be used include orthopedics, urology, gastroenterology, and thoracic & pulmonary surgery.

Ophthalmic uses include treatment of glaucoma, age-related macular degeneration (AMD), proliferative diabetic retinopathy, retinopathy of prematurity, retinal tear and detachment, retinal vein occlusion, and/or refractive surgery treatment to reduce or eliminate refractive errors.

Veterinary uses include both small animal and large animal procedures.

Examples of dental applications include hard tissue, soft tissue, and endodontic procedures. Hard tissue dental procedures include caries removal & cavity preparation and laser etching. Soft tissue dental procedures include incision, excision & vaporization, treatment of gummy smile, coagulation (hemostasis), exposure of unerupted teeth, aphthous ulcers, gingivoplasty, gingivectomy, gingival troughing for crown impressions, implant exposure, frenectomy, flap surgery, fibroma removal, operculectomy, incision & drainage of abscesses, oral papilectomy, reduction of gingival hypertrophy, pre-prosthetic surgery, pericoronitis, peri implantitis, oral lesions, and sulcular debridement. Endodontic procedures include pulpotomy, root canal debridement, and cleaning. Dental procedures also include tooth whitening.

Generally, the type of laser, wavelength, fiber length, fiber outer diameter, and fiber inner diameter, among other system parameters, are selected according to the application. For example, embodiments in which the laser is a $CO_2$ laser, the laser system can be used for surgical procedures requiring the ablation, vaporization, excision, incision, and coagulation of soft tissue. $CO_2$ laser systems can be used for surgical applications in a variety of medical specialties including aesthetic specialties (e.g., dermatology and/or plastic surgery), podiatry, otolaryngology (e.g., ENT), gynecology (including laparoscopy), neurosurgery, orthopedics (e.g., soft tissue orthopedics), arthroscopy (e.g., knee arthroscopy), general and thoracic surgery (including open surgery and endoscopic surgery), dental and oral surgery, ophthalmology, genitourinary surgery, and veterinary surgery.

In some embodiments, $CO_2$ laser systems can be used in the ablation, vaporization, excision, incision, and/or coagulation of tissue (e.g., soft tissue) in dermatology and/or plastic surgery in the performance of laser skin resurfacing, laser derm-abrasion, and/or laser burn debridement. Laser skin resurfacing (e.g., by ablation and/or vaporization) can be performed, for example, in the treatment of wrinkles, rhytids, and/or furrows (including fine lines and texture irregularities). Laser skin resurfacing can be performed for the reduction, removal, and/or treatment of: keratoses (including actinic keratosis), seborrhoecae vulgares, seborrheic wart, and/or verruca seborrheica; vermillionectomy of the lip; cutaneous horns; solar/actinic elastosis; cheilitis (including actinic cheilitis); lentigines (including lentigo maligna or Hutchinson's malignant freckle); uneven pigmentation/dyschromia; acne scars; surgical scars; keloids (including acne keloidalis nuchae); hemangiomas (including Buccal, port wine and/or pyogenic granulomas/granuloma pyogenicum/ granuloma telagiectaticum); tattoos; telangiectasia; removal of skin tumors (including periungual and/or subungual fibromas); superficial pigmented lesions; adenosebaceous hypertrophy and/or sebaceous hyperplasia; rhinophyma reduction; cutaneous papilloma; milia; debridement of eczematous and/ or infected skin; basal and squamous cel carcinoma (including keratoacanthomas, Bowen's disease, and/or Bowenoid Papulosis lesions); nevi (including spider, epidermal, and/or protruding); neurofibromas; laser de-epithelialization; tricoepitheliomas; xanthelasma palpebrarum; and/or syringoma. $CO_2$ laser systems can be used for laser ablation, vaporization and/or excision for complete and/or partial nail matrixectomy, for vaporization and/or coagulation of skin lesions (e.g., benign and/or malignant, vascular and/or avascular), and/or for Moh's surgery, for lipeci omy. Further examples include using laser system 1300 for laser incision and/or excision of soft tissue for the performance of upper and/or lower eyelid blepharoplasty, and/or for the creation of recipient sites for hair transplantation.

In certain embodiments, $CO_2$ laser systems is used in the laser ablation, vaporization, and/or excision of soft tissue during podiatry procedures for the reduction, removal, and/or treatment of: verrucae vulgares/plantar warts (including paronychial, periungual, and subungual warts); porokeratoma ablation; ingrown nail treatment; neuromas/fibromas (including Morton's neuroma); debridement of ulcers; and/or other soft tissue lesions. $CO_2$ laser systems can also be used for the laser ablation, vaporization, and/or excision in podiatry for complete and/or partial matrixectomy.

$CO_2$ laser systems can be used for laser incision, excision, ablation, and/or vaporization of soft tissue in otolaryngology for treatment of: choanal atresia; leukoplakia (including oral, larynx, uvula, palatal, upper lateral pharyngeal tissue); nasal obstruction; adult and/or juvenile papillomatosis polyps; polypectomy of nose and/or nasal passages; lymphangioma removal; removal of vocal cord/fold nodules, polyps and cysts; removal of recurrent papillomas in the oral cavity, nasal cavity, larynx, pharynx and trachea (including the uvula, palatal, upper lateral pharyngeal tissue, tongue and vocal cords); laser/tumor surgery in the larynx, pharynx, nasal, ear and oral structures and tissue; Zenker' diverticulum/pharynoesophageal diverticulum (e.g., endoscopic laser-assisted esophagodiverticulostomy); stenosis (including subglottic stenosis); tonsillectomy (including tonsillar cryptolysis, neoplas ma) and tonsil ablation/tonsillotomy; pulmonary bronchial and tracheal lesion removal; benign and malignant nodules, tumors and fibromas (e.g., of the larynx, pharynx, trachea, tracheobronchial/endobronchial); benign and/or malignant lesions and/or fibromas (e.g., of the nose or nasal passages); benign and/or malignant tumors and/or fibromas (e.g., oral); stapedotomy/stapedectomy; acoustic neuroma in the ear; superficial lesions of the ear (including chondrodermatitis nondularis chronica helices/Winkler's disease); telangiectasia/hemangioma of larynx, pharynx, and/or trachea (including uvula, palatal, and/or upper lateral pharyngeal tissue); cordectomy, cordotomy (e.g., for the treatment of vocal cord paralysis/vocal fold motion impairment), and/or cordal lesions of larynx, pharynx, and/or trachea; myringotomy/tympanostomy (e.g., tympanic membrane fenestration); uvulopalatoplasty (e.g., LAUP); turbinectomy and/or turbinate reduction/ablation; septal spur ablation/reduction and/or septoplasty; partial glossectomy; tumor resection on oral, subfacial and/or neck tissues; rhinophyma; verrucae vulgares; and/or gingivoplasty/gingivectomy.

In some embodiments, $CO_2$ laser systems can be used for the laser incision, excision, ablation, and/or vaporization of soft tissue in gynecology for treatment of conizaton of the cervix (including cervical intraepithelial neoplasia, vulvar and/or vaginal intraepithelial neoplasia); condyloma acuminata (including cervical, genital, vulvar, preineal, and/or Bowen's disease, and/or Bowenoid papulosa lesions); leukoplakia (e.g., vulvar dystrophies); incision and drainage of Bartholin's and/or nubuthian cysts; herpes vaporization; urethral caruncle vaporization; cervical dysplasia; benign and/or malignant tumors; and/or hemangiomas.

$CO_2$ laser systems can be used for the vaporization, incision, excision, ablation and/or coagulation of soft tissue in endoscopic and/or laparoscopic surgery, including gynecology laparoscopy, for treatment of: endometrial lesions (inclusing ablation of endometriosis); excision/lysis of adhesions; salpingostomy; oophorectomy/ovariectomy; fimbroplasty; metroplasty; tubal microsurgery; uterine myomas and/or fibroids; ovarian fibromas and/or follicle cysts; uterosacral ligament ablation; and/or hysterectomy.

In certain embodiments, CO2 laser systems are used for the laser incision, excision, ablation, and/or vaporization of soft tissue in neurosurgery for the treatment of cranial conditions, including: posterior fossa tumors; peripheral neurectomy; benign and/or malignant tumors and/or cysts (e.g., gliomos, inenigiomas, acoustic neuromas, lipomas, and/or large tumors); arteriovenous malformation; and/or pituitary gland tumors. In some embodiments, $CO_2$ laser systems are used for the laser incision, excision, ablation, and/or vaporization of soft tissue in neurosurgery for the treatment of spinal cord conditions, including: incision/excision and/or vaporization of benign and/or malignant tumors and/or cysts; intra- and/or extradural lesions; and/or laminectomy/laminotomy/microdisectomy.

$CO_2$ laser systems can be used for the incision, excision, and/or vaporization of soft tissue in orthopedic surgery in applications that include arthroscopic and/or general surgery. Arthroscopic applications include: menisectomy; chondromalacia; chondroplasty; ligament release (e.g., lateral ligament release); excision of plica; and/or partial synovectomy. General surgery applications include: debridement of traumatic wounds; debridement of decubitis and/or diabetic ulcers; microsurgery; artificial joint revision; and/or polymer (e.g., polymethylmethacrylate) removal.

$CO_2$ laser systems can also be used for incision, excision, and/or vaporization of soft tissue in general and/or thoracic surgery, including endoscopic and/or open procedures. Such applications include: debridement of decubitus ulcers, stasis, diabetic and other ulcers; mastectomy; debridement of burns; rectal and/or anal hemorrhoidectomy; breast biopsy; reduction mammoplasty; cytoreduction for metastatic disease; laparotomy and/or laparoscopic applications; mediastinal and/or thoracic lesions and/or abnormalities; skin tag vaporization; atheroma; cysts (including sebaceous cysts, pilar cysts, and/or mucous cysts of the lips); pilonidal cyst removal and/or repair; abscesses; and/or other soft tissue applications.

In certain embodiments, $CO_2$ laser systems can be used for the incision, excision, and/or vaporization of soft tissue in dentistry and/or oral surgery, including for: gingivectomy; gingivoplasty; incisional and/or excisional biopsy; treatment of ulcerous lesions (including aphthous ulcers); incision of infection when used with antibiotic therapy; frenectomy; excision and/or ablation of benign and/or malignant lesions; homeostasis; operculectomy; crown lengthening; removal of soft tissue, cysts, and/or tumors; oral cavity tumors and/or hemangiomas; abscesses; extraction site hemostasis; salivary gland pathologies; preprosthetic gum preparation; leukoplakia; partial glossectomy; and/or periodontal gum resection.

In some embodiments, $CO_2$ laser systems can be used for incision, excision, and/or vaporization of soft tissue in genitourinary procedures, including for: benign and/or malignant lesions of external genitalia; condyloma; phimosis; and/or erythroplasia.

EXAMPLE

Surgery was performed to remove portions of the larynx from a dog using a $CO_2$ laser system operating at 10.6 microns. The photonic crystal fiber used in this procedure had a hollow core approximately 550 microns in diameter. The fiber had spiral confinement region that included a radial profile of approximately 20 $PES/As_2Se_3$ bilayers. The bilayer thickness was approximately 3 microns, with a thickness ration of approximately 2 to 1 (PES to $As_2Se_3$). The fiber's cladding was formed from PES, and the fiber's OD was approximately 1500 microns. The fiber was 1.5 m long.

A complete en bloc supraglottic laryngectomy was performed including a cordectomy. The laser radiation was delivered using the photonic crystal fiber with a semi-rigid hand-piece. The hand-piece was inserted through a rigid laryngoscope. The input power into the fiber was approximately 20 Watts. The radiation power exiting the fiber was approximately 7 Watts. Nitrogen was blown through the fiber in the same direction as the radiation. The nitrogen flow rate was approximately 1 liter/min.

Radiation was delivered to the target tissue with a few millimeters (e.g., about 5 mm-1 cm) standoff between the distal end of the fiber and the target tissue. The supraglottis was removed with just one pause to cauterize any incised blood vessels or to suction any blood away from the target area. Minimal bleeding was observed, with blood from incised vessels coagulating as it was exposed to the output from the fiber. The procedure lasted about 45 minutes, during which time the supraglottis and left cord were removed from the dog.

ADDITIONAL EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. An medical laser system for delivering laser radiation to a patient, comprising:
    a laser configured to provide radiation at a wavelength $\lambda$; and
    a conduit configured to deliver radiation at a wavelength $\lambda$ from the laser to a target location of the patient, the conduit comprising:
    a photonic crystal fiber waveguide extending along a waveguide axis, the photonic crystal fiber waveguide being a flexible waveguide having a hollow core, the photonic crystal fiber waveguide being configured to guide the radiation at $\lambda$ through the core along the waveguide axis; and
    a second optical waveguide extending along the waveguide axis, the second optical waveguide being coupled to the photonic crystal fiber waveguide to deliver the radiation to or receive the radiation from the photonic crystal fiber waveguide,
    wherein the second optical waveguide is a non-photonic crystal fiber waveguide and the second optical waveguide has a hollow core.

2. The medical laser system of claim 1, wherein the second optical waveguide is a hollow metallic waveguide.

3. The medical laser system of claim 1, wherein the photonic crystal fiber comprises an all-dielectric confinement region surrounding the hollow core.

4. The medical laser system of claim 3, wherein the dielectric confinement region comprises a layer of a first dielectric material arranged in a spiral around the waveguide axis.

5. The medical laser system of claim 4, wherein the first dielectric material is a chalcogenide glass.

6. The medical laser system of claim 4, wherein the dielectric confinement region further comprises a second dielectric material arranged in a spiral around the waveguide axis.

7. The medical laser system of claim 6, wherein the first dielectric material is an inorganic glass and the second dielectric material is a polymer.

8. The medical laser system of claim 1, wherein the photonic crystal fiber waveguide is sufficiently flexible to guide the radiation to the target location while a portion of the photonic crystal fiber waveguide is bent through an angle of about 90 degrees or more and the portion has a radius of curvature of about 12 centimeters or less.

9. The medical laser system of claim 8, wherein the radiation has an average power at the output end of about 1 Watt or more while the portion of the photonic crystal fiber waveguide is bent through an angle of about 90 degrees or more and the portion has a radius of curvature of about 12 centimeters or less.

10. The medical laser system of claim 1, wherein the laser is a $CO_2$ laser.

11. The medical laser system of claim 1, wherein the laser is an Nd:YAG laser or an Er:YAG laser.

12. The medical laser system of claim 1, wherein $\lambda$ is about 2,000 nm or more.

13. The medical laser system of claim 1, wherein $\lambda$ is 10.6 μm.

* * * * *